US010842932B1

(12) United States Patent
Bibian et al.

(10) Patent No.: US 10,842,932 B1
(45) Date of Patent: Nov. 24, 2020

(54) INTELLIGENT PHARMACEUTICAL DELIVERY SYSTEM WITH NON-CONCENTRIC PUMPING MECHANISM TO REDUCE FLOW ANOMALY AND METHOD OF USING

(71) Applicants: Stéphane Bibian, Cleveland Heights, OH (US); Sankar Barua, Stow, OH (US); Tatjana Zikov, Cleveland Heights, OH (US)

(72) Inventors: Stéphane Bibian, Cleveland Heights, OH (US); Sankar Barua, Stow, OH (US); Tatjana Zikov, Cleveland Heights, OH (US)

(73) Assignee: NeuroWave Systems Inc., Cleveland Heights, OH (US)

(*) Notice: Subject to any disclaimer, the term of this patent is extended or adjusted under 35 U.S.C. 154(b) by 862 days.

(21) Appl. No.: 15/213,489

(22) Filed: Jul. 19, 2016

Related U.S. Application Data

(63) Continuation-in-part of application No. 14/874,736, filed on Oct. 5, 2015, now Pat. No. 10,130,766, which
(Continued)

(51) Int. Cl.
*F04B 43/12* (2006.01)
*A61M 5/142* (2006.01)
(Continued)

(52) U.S. Cl.
CPC ...... *A61M 5/1684* (2013.01); *A61M 5/14232* (2013.01); *A61M 19/00* (2013.01);
(Continued)

(58) Field of Classification Search
CPC .. F04B 43/12; F04B 43/1238; F04B 43/1253; F04B 45/08; F04B 9/02; F04B 17/03;
(Continued)

(56) References Cited

U.S. PATENT DOCUMENTS 4,185,949 A 1/1980 Maguire
4,500,269 A 2/1985 Jess
(Continued)

*Primary Examiner* — Bhisma Mehta
*Assistant Examiner* — William R Frehe
(74) *Attorney, Agent, or Firm* — Brian Kolkowski

(57) ABSTRACT

The present invention relates to the titration and delivery of anesthetic and sedative medications to a subject. Further, the present invention relates to a device and methods for titrating and delivering such medications in a semi-automated or fully automated manner and which can be monitoring and controlled remotely. Even still further, the present invention relates to such a device that can perform the titration and delivery of medication in a manner that minimalizes occlusion and prevents back flow of the medication. More particularly, the present invention relates to a device for titration and delivery of medication using a non-concentric pumping mechanism that gradual or progressively increases and decreases occlusion in the medication delivery line within the pump to minimize and/or prevent sudden formation and release of occlusion in order to provide more steady and continuous flow of the medication through the device to the subject.

6 Claims, 4 Drawing Sheets

Related U.S. Application Data is a continuation-in-part of application No. 13/962,565, filed on Aug. 8, 2013.

(60) Provisional application No. 61/680,888, filed on Aug. 8, 2012, provisional application No. 62/338,129, filed on May 18, 2016.

(51) Int. Cl.
*A61M 5/168* (2006.01)
*A61M 19/00* (2006.01)
*G08B 5/36* (2006.01)

(52) U.S. Cl.
CPC .............. *F04B 43/12* (2013.01); *G08B 5/36* (2013.01); *A61M 2005/16863* (2013.01); *A61M 2205/14* (2013.01); *A61M 2205/18* (2013.01); *A61M 2205/332* (2013.01); *A61M 2205/6063* (2013.01); *A61M 2230/005* (2013.01); *A61M 2230/10* (2013.01); *F04B 43/1238* (2013.01); *F04B 43/1253* (2013.01)

(58) Field of Classification Search
CPC ...... F04B 43/04; F04B 43/09; F04B 43/1276; A61M 39/26; A61M 39/28; A61M 39/285; A61M 39/286; A61M 5/14228; A61M 5/14232
USPC ..... 417/477.6, 410.1, 474, 476–477.3, 477.9
See application file for complete search history.

(56) References Cited

U.S. PATENT DOCUMENTS

| | | | | |
|---|---|---|---|---|
| 4,522,571 | A | 6/1985 | Little | |
| 4,559,040 | A | 12/1985 | Horres et al. | |
| 4,954,046 | A | 9/1990 | Irvin et al. | |
| 5,037,274 | A * | 8/1991 | Holmes | F04B 43/1253 417/475 |
| 5,558,507 | A | 9/1996 | Magnus | |
| 6,102,678 | A * | 8/2000 | Peclat | A61M 5/142 417/474 |
| 6,267,570 | B1 | 7/2001 | Armando | |
| 6,523,414 | B1 * | 2/2003 | Malmstrom | A61M 5/16854 73/705 |
| 6,948,638 | B2 * | 9/2005 | Tu | A47K 5/1215 222/102 |
| 7,217,108 | B2 | 5/2007 | Herwig et al. | |
| 8,905,731 | B2 * | 12/2014 | Baron | F04B 43/1223 417/477.6 |
| 10,130,766 | B1 * | 11/2018 | Bibian | A61M 5/1723 |
| 2003/0113220 | A1 | 6/2003 | Cull | |
| 2004/0079372 | A1 * | 4/2004 | John | A61B 5/746 128/204.18 |
| 2004/0193068 | A1 * | 9/2004 | Burton | A61B 5/0476 600/544 |
| 2006/0047538 | A1 * | 3/2006 | Condurso | G06F 19/3456 705/3 |
| 2009/0162228 | A1 * | 6/2009 | Nelson | F04B 43/1253 417/477.2 |
| 2011/0295196 | A1 * | 12/2011 | Chazot | A61M 5/1723 604/66 |
| 2012/0184892 | A1 * | 7/2012 | Bigler | A61M 1/1037 604/9 |
| 2013/0177463 | A1 * | 7/2013 | Cheng | F04B 43/1261 417/477.1 |
| 2013/0189120 | A1 | 7/2013 | Nelson et al. | |
| 2016/0017880 | A1 * | 1/2016 | Maguire | F04B 49/06 417/410.3 |
| 2016/0106630 | A1 * | 4/2016 | Hudson | F04B 43/12 700/282 |

\* cited by examiner

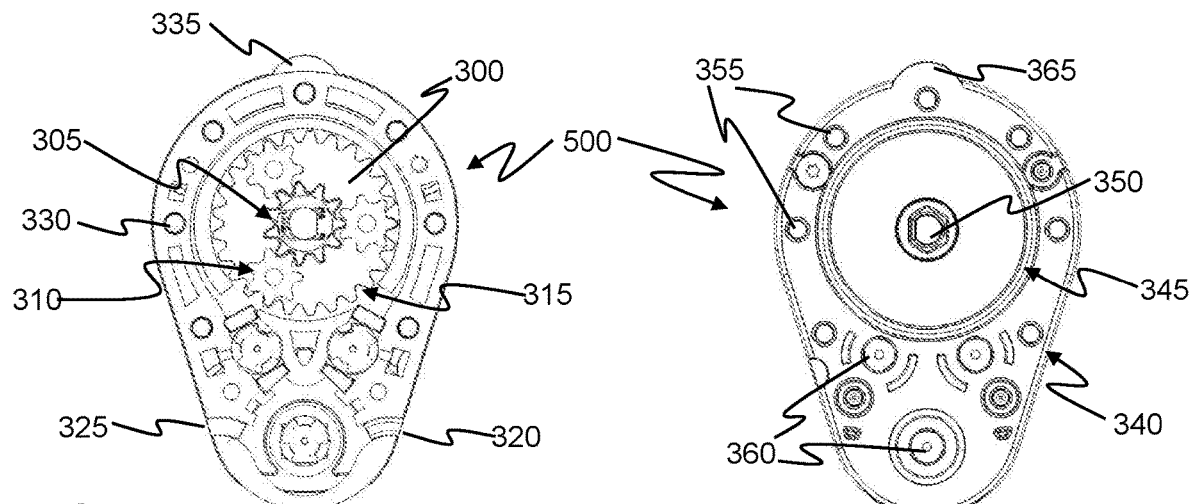
FIG. 3A
FIG. 3B
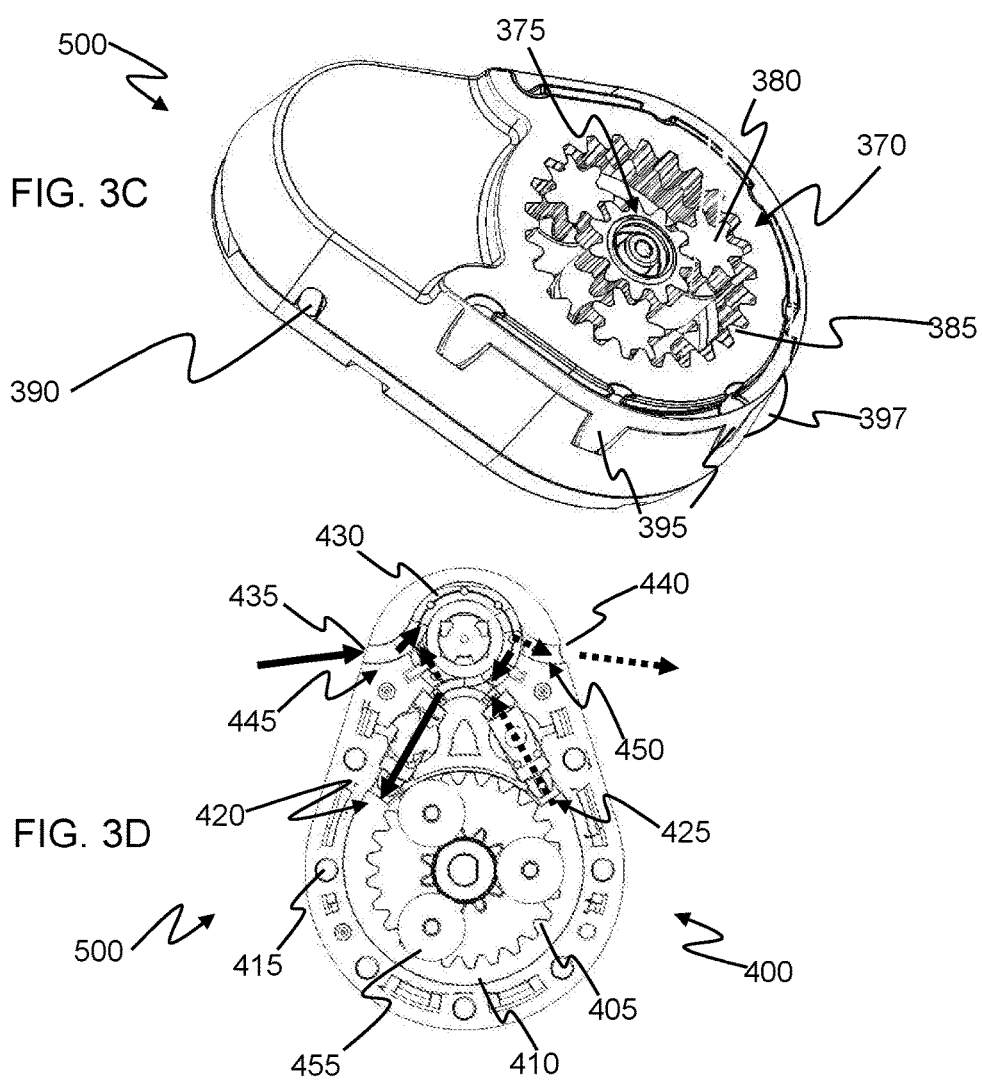
FIG. 3C
FIG. 3D

INTELLIGENT PHARMACEUTICAL DELIVERY SYSTEM WITH NON-CONCENTRIC PUMPING MECHANISM TO REDUCE FLOW ANOMALY AND METHOD OF USING

CROSS-REFERENCE TO RELATED APPLICATION

This application claims priority as a continuation-in-part of U.S. patent application Ser. No. 14/874,736, filed on Oct. 5, 2015, which was a continuation-in-part of U.S. patent application Ser. No. 13/962,565, which was filed Aug. 8, 2013, and which claims priority to provisional U.S. Patent Application Ser. No. 61/680,888 filed on Aug. 8, 2012. This application further claims priority to Provisional U.S. Patent Application No. 62/338,129 filed on May 18, 2016.

LICENSE RIGHTS-FEDERAL SPONSORED RESEARCH

The U.S. Government has a paid-up license in this invention and the right in limited circumstances to require the patent owner to license others on reasonable terms provided for by the terms of contract number N00014-14-C-0324 awarded by the Office of Naval Research.

BACKGROUND OF THE INVENTION

1. Field of the Invention

The present invention relates to the titration and delivery of medication to a subject. More particularly, the present invention relates to the titration and delivery of anesthetic and sedative medications to a subject. Further, the present invention relates to a device and methods for titrating and delivering such medications in a semi-automated or fully automated manner. Still further the present invention relates to such a device that can be monitored and controlled remotely. Even still further, the present invention relates to such a device that can perform the titration and delivery of medication in a manner that minimalizes occlusion and prevents back flow of the medication. More particularly, the present invention relates to a device for titration and delivery of medication using a non-concentric pumping mechanism that gradually or progressively increases and decreases occlusion in the medication delivery line within the pump to minimize and/or prevent sudden formation and release of occlusion in order to provide more steady and continuous flow of the medication through the device to the subject.

2. Technical Background

There exists an established and unmet need for providing enhanced capabilities in forward surgical, combat casualty care, and en-route care as well as in stationary civilian and critical care settings. Over the past 70 years, there have been attempts to use the electrical brain activity as a monitor of anesthetic depth. With increasing depth of sedation, the EEG shows a common progression from low-amplitude/high-frequency signal to high-amplitude/low-frequency signal, and finally to isoelectricity (i.e., flat signal characteristic of pharmacological coma), also known as burst suppression. Changes in EEG signals following the administration of drugs, ischemic episodes, changes in perfusion, etc., tend to occur rapidly. In order to detect them in a timely manner, trained EEG technologists must interpret the EEG signals in real-time and make rapid decisions based on their expertise. This is a particularly time consuming task, reserved only for a few specific clinical applications, such as the detection of ischemia during carotid endarterectomy, or the detection of ictal activity in the long-term EEG monitoring units in epileptic patients. Raw EEG signals are typically of little value to anesthesiologists and critical care physicians, as they lack the expertise and time required for their interpretation.

Since the late 1990s, a number of processed EEG monitors have been developed to simplify the interpretation of complex EEG signals, hence providing anesthesiologists with an additional, more direct means for drug effect assessment. The use of such monitors for drug titration to achieve optimal depth of anesthesia has been shown to improve the quality of anesthetic regimen, leading to a number of advantages directly related to patient outcome, e.g., (a) avoidance of excessive depth of anesthesia, (b) avoidance of intraoperative awareness, (c) reduction in post-operative recovery times, less post-operative and ICU delirium and less time spent on a ventilator in the ICU with lesser incidence of related pulmonary infections, (d) reduction in post-operative nausea and vomiting, and (e) reduction in duration of post-operative care units stay. Additionally, using such monitors, clinicians are able to manually adjust the amount of drugs administered in order to reduce the incidence of under- and over-dosing. In fact, the use of brain function monitors has been shown to help clinicians decrease the overall amount of drug administered to their patients, which in turn leads to faster wake up and discharge time, in addition to the other benefits for patient outcome listed above. Recent research has also shown that maintaining patients at too deep anesthetic levels is associated with an increased cognitive decline and post-operative mortality rate, which can be ameliorated with brain function monitoring.

At least one recent study has shown that a brain-monitored group showed a 78 percent reduction in patient recall of unpleasant experiences as compared to the standard practice group, along with an 18 percent decrease in cost of sedative drugs. In addition, the use of brain function monitors in chemically sedated patients has been found to facilitate the conflicting goals of maintaining sedation and safely interrupting sedation to perform a neurological examination. Today, there is a high incidence of oversedation in ICUs (40 percent to 60 percent of patients). Oversedation in the ICU is a serious problem, resulting in delayed weaning from mechanical ventilation, which lengthens ICU stay and significantly increases patient risks and healthcare costs. In 2003, prolonged mechanical ventilation (≥96 hours) occurred in about 300,000 cases, and accounted for nearly 7 million additional hospital days and $16 billion in hospital costs annually, projected to more than double by 2020.

Further, in spite of the advancements that have been made in anesthesia and sedation with the inclusion of brain monitoring, these systems are still relegated to mainly to surgical suites and the like. There is currently no sedation or anesthetic system utilizing brain monitoring which can be used in a setting other than a stationary one such as hospital operating room or similar facility.

More generally, peristaltic pumps for anesthesia and sedative delivery typically exhibit many issues that make administration of such compounds problematic. Such systems currently known in the art typically are prone to flow pulsation caused by the build-up and release of occlusion in the pump line. Such pumps known in the art typically maintain a constant level of occlusion in the pump line throughout the entire length of the tube within the pump, and then at the point where the tube exits the pump the occlusion is released suddenly and completely which causes the pump line or tube to spring open and allow the anesthesia or sedative to rapidly exit the pump and flow toward the subject, but leaves an empty portion of the pump line which acts as a vacuum. This can cause backflow in the pump line. The flow pulsation leads to inconsistent delivery of anesthesia or sedative to the subject and can cause further problems if the backflow is severe or unmitigated.

In light of the above, it is therefore an object of the present invention to provide a semi-closed-loop or closed-loop anesthesia or sedation system. It is further an object of the present invention to provide such a system capable of being applied even by a person with minimal training, and requiring no continuous human interaction or continuous human presence at the bedside. It is still further an object of the present invention to provide a system for semi-closed-loop or closed-loop anesthesia or sedation which is capable of determining unsafe levels of anesthesia or sedation as well as unsafe brain activity, such as burst suppression, and controlling the level of anesthetic or sedative being delivered based on those determinations. It is yet another object of the present invention to provide a system and method for controlling anesthesia or sedation in the field, at the point of injury (POI), or during transport between the POI and upper echelons of care (e.g., hospital, surgical suite, etc.), in addition to all echelons of care, including civilian care facilities including but not limited to operating rooms, emergency rooms and intensive care units. It is still further an object of the present invention to provide an anesthesia or sedation delivery device that provides consistent, steady flow of the anesthesia or sedative compound while minimizing or eliminating flow pulsation and/or back flow within the pump lines.

SUMMARY OF THE INVENTION

The present invention relates to the titration and delivery of medication to a subject. More particularly, the present invention relates to the titration and delivery of anesthetic and sedative medications to a subject. Further, the present invention relates to a device and methods for titrating and delivering such medications in a semi-automated or fully automated manner. Still further the present invention relates to such a device that can be monitored and controlled remotely. Even still further, the present invention relates to such a device that can perform the titration and delivery of medication in a manner that minimalizes occlusion and prevents back flow of the medication. More particularly, the present invention relates to a device for titration and delivery of medication using a non-concentric pumping mechanism that gradually or progressively increases and decreases occlusion in the medication delivery line within the pump to minimize and/or prevent sudden formation and release of occlusion in order to provide more steady and continuous flow of the medication through the device to the subject. The present invention further relates to the monitoring and processing of signals, and particularly to the monitoring and processing of electrophysiological signals. More particularly, the present invention relates to processing electroencephalographic (EEG) signals to monitor brain function. Even more particularly, the present invention relates to a system and method for. Further still, the present invention relates to a system, as described above, for controlling sedation or anesthesia for transportation or evacuation of the injured as well as closed-loop sedation or anesthesia at all echelons of care, including civilian and critical care facilities. The present invention further relates to systems and methods for controlling anesthesia or sedation of a subject in stationary care facilities, such as the ICU or surgical settings, and possibly where the subject is on a ventilator. The system collects electroencephalographic (EEG) signals from a subject and utilizes various novel algorithms to analyze and quantify those EEG signals, or at least portions thereof, to monitor the subject. It should be noted that the EEG signals acquired by the system also contain electromyographic and electro-oculographic information. Many aspects of the subject's brain function can be monitored, including, but not limited to, monitoring the occurrence of seizures, occurrence of brain hypoperfusion or ischemia, alertness, sleep architecture and quality, cognition, memory, brain functional (or neuronal) connectivity, state of consciousness, EEG slowing, loss of EEG amplitude, cortical suppression, and the like. The system can also monitor the EEG for the presence of artifacts, like environmental extraneous noise, or physiological noise (e.g., muscle activity, movements, ocular activity, etc.).

The present invention includes many embodiments utilizing a peristaltic pump for delivery of, at least, anesthetic or sedative compounds to a subject. Preferably, the pump includes numerous advanced features capable of ensuring consistent delivery of said compounds to the subject. The peristaltic pumps in the many embodiments of the present invention preferably are adapted to provide a progressive occlusion release. Progressive occlusion release allows the pump to gradually decrease occlusion in the pump line, as opposed to the sudden and complete release in typical pumps known in the art. Preferably, the pump of the present invention progressively and gradually reduces occlusion prior to the point at which the tube exits the pump. By progressively reducing occlusion, it means that preferably, occlusion is reduced gradually and steadily as the tube nears the exit point, though it may be released in a step-wise fashion characterized by a series of changes in the level of occlusion. It is preferable, however, to continuously reduce occlusion from the maximum level to a minimum level at a steady and progressive rate without step-wise changes. Most preferably, occlusion is decreased linearly in that it decreases at a steady, linear rate from its maximum value to a minimum value that is negative indicating that the roller is not causing any occlusion at all. The smooth and continuous release of occlusion further helps to minimize flow pulsation and other disturbances in flow. On the entry side, occlusion is preferably increased quickly to a minimum value of about 5% as the tubing enters the administration set/cartridge which serves to prevent backflow of the fluid or medication in the tube. This minimum occlusion percentage on the entry side, provided by what can be called a "pulling roller" (i.e., the roller or roller element that has most recently entered the pumping chamber and is acting to pull fluid or medication from the source into the tubing), can be maintained as long as the "pushing roller" (i.e., the roller or roller element approaching the exit opening of the administration set/cartridge and acting to push the fluid or medication out of the pump and toward the subject) maintain sufficient occlusion. Once occlusion of the pushing roller is decreased to a low enough value, the occlusion value of the pulling roller is increased, preferably progressively (in the opposite direction, but similar as described for occlusion decrease) to reach the maximum value. Disturbances in flow are not limited to such backflow; peristaltic pumps may further be prone to stoppage of flow entirely. This is particularly dangerous as consistent flow of some rate is important to help prevent collapsing of the subject's vein or artery. The pulsation anomaly typically corresponds to the passage of the roller where the tubing exits the casing of the pump head. As the roller passes over that point, the tubing occlusion prevents any fluid to be pushed into the tube. As such, the flow stops. It has been determined that at a flow rate of 31.76 mL/hr, the flow anomaly lasts about 3 seconds. At 1 mL/hr (the 'keep vein open' rate), the anomaly can last up to 100 seconds. This is the time during which no fluid is being delivered to the patient to keep the vein open. During that time, there is an increased risk of having the vein closing, which would prevent further drug administration once the roller clears the anomaly region. Thus, the present invention's ability to reduce or eliminate these flow anomalies and progressively decrease occlusion serve to more consistently and safely administer fluids or medications via such pumps. One way to characterize the release of occlusion is by the rate of decrease from maximum levels. Preferably, occlusion is decreased by approximately 20% for every 10 degrees of rotation of the pump. More preferably, occlusion is decreased by 15% for every 10 degrees of rotation of the pump. Still more preferably, occlusion is decreased by 10% for every 10 degrees of rotation of the pump. Yet more preferably, occlusion is decreased by 5% for every 10 degrees of rotation of the pump. Most preferably, occlusion is decreased continuously and steadily from the maximum level of occlusion to the exit point. Another way to characterize the decrease in occlusion is in relation to the pump itself. Maximum occlusion may be reached at the entry point where the tube enters the pump, or occlusion may be gradually increased from the entry point to any given point where occlusion reaches its maximum value. However, the present invention focuses on beginning to release occlusion prior to the exit point where the tube exits the pump, and reaching a minimum occlusion level at or before this exit point. Occlusion may begin to be decreased at any point prior to the exit point, so long as occlusion is minimal at the point where the tube exits the pump. Preferably, at the exit point, occlusion is at most 20% of the maximum occlusion level. More preferably, at the exit point, occlusion is at most 15% of the maximum occlusion level. Still more preferably, at the exit point, occlusion is at most 10% of the maximum occlusion level. Yet more preferably, at the exit point, occlusion is at most 5% of the maximum occlusion level. Even more preferably, at the exit point, occlusion is at most 0% of the maximum occlusion level. Another way to characterize occlusion at the exit point is in terms of overall occlusion percentage. Preferably, occlusion is at most 10% prior to or at the exit point. More preferably, occlusion is at most 7% prior to or at the exit point. Yet more occlusion is at most 5% prior to or at the exit point. Still more preferably, occlusion is at most 3% prior to or at the exit point. Even more preferably, occlusion is at most 0% prior to or at the exit point. Most preferably, the occlusion percentage is a negative value prior to or at the exit point which means the pump is not compressing the pump line or tube at all and the line or tube is fully open.

Many embodiments of the system include a brain function monitor. The system or monitor may, in many embodiments be small, possibly miniaturized, optionally portable and possibly even disposable. The system or monitor should preferably be capable of use by even non-experts. By this, it is meant that a person should not be required to possess extraordinary or specialized medical training in order to be easily taught to use the system effectively and reliably. The system should therefore preferably be automatic in operation in a number of respects. First, the system should be capable of automatic calibration of its electronic circuits, their gains, filters and the like components and features in order to maintain the accurate signal acquisition and analysis without the need for human supervision of the instrumentation during the entire course of employment. Second, the system should preferably have automatic detection of poor electrode impedance, disconnected leads, and input signal quality; for example, the system should also be capable of detecting an imbalance in electrode impedances, physiological and environmental artifacts, and electrical and magnetic interferences and noise, including those due to electrostatic fields and discharges. Third, the system should preferably be capable of artifact detection and removal on one or more levels, so as to isolate, identify or recover for analysis that part of the signal which conveys meaningful information related to a subject's brain or cortical activity pertaining to: level of consciousness; occurrence of a seizure; level of sedation or depth-of-anesthesia; brain functional (or neuronal) connectivity that, for example, can be affected by diseases such as Parkinson's and Alzheimer's; occurrence of brain hypoperfusion; brain ischemia or impaired cerebral blood flow; brain death or dysfunction or impairment; brain metabolic demand; sleep disorders; sleep architecture and quality; alertness and cognition, memory; hypo- and hyperglycemia; psychiatric disorders such as depression, ADHD, autism, OCD, etc.; person's intentions, truthfulness or substance abuse; use in brain-computer interfaces such as for control of artificial prosthetics or dysfunctional body parts or objects or devices such as robots, game consoles, vehicles and the like; and use for detection or control of another person's or one's own thought or physiologic processes. Fourth, the system should preferably include output devices to provide outputs which result in visual and/or audible feedback capable of informing the user of the state of the patient related to quantification of brain or cortical activity, level of consciousness, occurrence of a seizure, level of sedation and the like as previously mentioned, at any time during the period of time that the system was monitoring the patient.

Preferably, the system should operate in real time. One example of real-time operation is the ability of the system to monitor the subject's physiological signals and provide quantitative analysis about the subject's status substantially simultaneously as the signals are acquired. Another example of real-time operation includes the ability to detect a seizure or brain dysfunction event, or other pathologic or nonpathologic brain event essentially as it is happening, rather than being limited to analysis that takes place several seconds, minutes or hours afterward. Preferably, by real-time detection, it is meant that the system operates to detect brain dysfunction or injury within 3 minutes of application of the system and/or occurrence of the dysfunction or injury. More preferably, the system operates to detect brain dysfunction or injury within 1 minute of application of the system and/or occurrence of the dysfunction or injury. Still more preferably, the system operates to detect brain dysfunction or injury within 30 seconds of application of the system and/or occurrence of the dysfunction or injury. Yet more preferably, the system operates to detect brain dysfunction or injury within 15 seconds of application of the system and/or occurrence of the dysfunction or injury. Even more preferably, the system operates to detect brain dysfunction or injury within 10 seconds of application of the system and/or occurrence of the dysfunction or injury. Still yet more preferably, the system operates to detect brain dysfunction or injury within 5 seconds of application of the system and/or occurrence of the dysfunction or injury. Still even more preferably, the system operates to detect brain dysfunction or injury within 1 second of application of the system and/or occurrence of the dysfunction or injury. Most preferably, the system operates to detect brain dysfunction or injury substantially instantaneously upon application of the system and/or occurrence of the dysfunction or injury. The system further operates in real-time with respect to monitoring of the subject's physiological signals such that there is substantially no lag or delay between the body's production of the signal, and the system's monitoring of the signal. The system described in this invention also preferably incorporates a number of unique features that improve safety, performance, durability, and reliability. The system should be cardiac defibrillator proof or other electric shock proof, meaning that its electrical components are capable of withstanding the surge of electrical current associated with the application of a cardiac defibrillator or other electric shock to a patient being monitored by the system, and that the system remains operable after sustaining such a surge. The system should have shielded leads so as to reduce as much as possible the effects of external electromagnetic interference on the collection of biopotentials or physiological signals from the patient being monitored by the system. The system should be auto-calibrating, more preferably capable of compensating for the potential differences in the gains of the different acquisition channels or in the impedances of the input electrodes.

Many embodiments of the brain function monitor include a sensing system comprising an electrode array or separate, individual electrodes, and in some embodiments a brain function monitor embedded within such an array. Preferably, at least two electrodes are utilized, comprising a monitoring electrode and a ground electrode. Alternatively, at least four electrodes may be utilized. In the four electrode array, preferably two electrodes are for monitoring EEG signals in the fronto-temporal region, one reference electrode is for providing a common reference signal, and one electrode is for grounding. Other electrode arrangements including larger number of electrodes, configurations, and placements are also contemplated for use with the system. Such electrode montages may or may not include a subset of 10-20 electrode placement system, or may go beyond it in both electrode locations and their number.

The electrodes used, when either separate electrodes or when part of an array, may be any of those commonly known in the art of EEG monitoring. The electrodes preferably do not require the application of conductive paste or gel. Therefore, the electrode lead or array preferably has any necessary conductive fluids pre-applied, or, more preferably, is a dry physiological electrode requiring no conductive fluid at all. Alternatively or in addition, the electrode is a wet-dry hybrid electrode as disclosed in U.S. Pat. No. 8,594,763 (which application is entirely incorporated by reference) and the like. The electrode lead or array may be affixed to or embedded into a flexible, wearable substrate or apparatus, which can be applied directly to the injured subject's head or other body part, preferably the forehead. Preferably, the substrate is designed to be flexible, easy to don and doff, and disposable yet still resilient and capable of withstanding forces common in emergency settings such as excessive vibration, movement, electric noise, EMI, electric and mechanical shock, and the like, in addition to such forces present to a lesser degree in non-emergency settings. The apparatus may be secured about the subject's head or other body part by means commonly known to those in the art, including, but not limited to, a cap or other garment or garment attachment completely encompassing the subject's head, a strap that is secured by compression or elastic means, or may utilize common fastening methods such as hook-and-loop, belt-type, snap connectors, or the like. Additionally, or in conjunction with one of the above means, an adhesive layer may be used in conjunction with a wearable apparatus to further ensure a stable, secure placement of the electrodes. In a preferred embodiment, the flexible substrate is a small patch-type or adhesive bandage (BAND-AID-type) garment comprising an adhesive layer which, when applied to the injured subject's forehead, is capable of maintaining a secure placement with minimal shifting, drift, or other movement of the apparatus, for the entire length of time necessary for monitoring. The adhesive layer is also preferably capable of providing a secure, stable attachment to the subject in the presence of dirt, sweat, and other detritus which may be covering the subject's skin during application, without the need for washing, cleaning or otherwise preparing the area of application. Preferably, in the preferred embodiments where the electrode array is integrated in the flexible substrate, the patch is small and easily applied, and integrates the acquisition electronics in the form of a few integrated circuits (ICs) or chipsets whose role is to amplify, filter, digitize, analyze, process, store or transmit, optionally wirelessly, the EEG and QEEG analog or converted digital signals. Preferably, the integrated electronics are small and inexpensive, such that the array is cost effective, such that it can be fully disposed of after use, minimizing the need for maintenance and re-shelving, or refurbishing. Preferably, the flexible substrate also embeds a connector, which allows it to be connected to a monitoring device comprising a display device. Such monitoring/display device can provide the necessary power to the flexible substrate electronics, and can perform all other necessary processing and displaying of the results.

In many embodiments, the monitoring/display device is small, rugged, and easily transportable. Also optionally, both the device and the display device may be constructed to be inexpensive and disposable. In many embodiments, the display comprises internal memory for recording the monitored EEG signals and the various processed signals and calculated values, indices, and the like for later analysis by a trained clinician. Also, in many embodiments, the display comprises an internal power source, such as a battery, that powers the device during monitoring and is sufficient to provide power at least until the injured subject can be transported to an upper echelon care location, at which point the device could be removed, data could be uploaded, and the monitor and display could be discarded. The display is preferably capable of depicting a variety of outputs from the brain function monitor, including, but not limited to, EEG signal waveforms, processed EEG signal waveforms, indices calculated by the system to indicate various aspects of the subject's brain function (e.g., suppression, seizure occurrence, state of consciousness, sedation or anesthesia level, subject's pain or analgesia level, occurrence of traumatic brain injury (TBI), sleep architecture and quality, alertness, cognition, brain functional connectivity, brain hypoperfusion, ischemia or metabolic demand, memory, brain death or impaired function, hypo- or hyperglycemia and the like).

In other embodiments, the display device can be a portable medical-grade computer system, providing a graphical user interface to view in real-time the acquired EEG signals, and review all processed quantitative EEG parameters.

Also, in some embodiments of the present invention, the display device or the device itself can communicate, optionally wirelessly, with other medical equipment, such as life signs monitors and drug delivery systems, or transmit the information to internet or upload it to a cloud, preferably in real time, for remote review, analysis or storage and the like. In some embodiments, the display device or the device itself can directly control one, two or more infusion pumps to deliver intravenous drugs to the patient. In one embodiment, a single infusion pump may be used to automatically adjust the infusion rate of a drug to provide and maintain a stable and suitable concentration of said drug in the injured subject's blood plasma. In many embodiments, the drug provided is a sedative or anesthetic drug, which is infused to maintain the subject at a stable sedation or anesthesia level with minimal or no human supervision. In many embodiments, alternatively, or in conjunction with the sedation or anesthetic drug, at least one (additional) infusion pump may be provided for infusion of analgesic medication to provide a stable and suitable level of pain relief or analgesia to the injured subject. In yet other embodiments, a third pump may be used to provide muscle relaxation medication. In other embodiments, additional pumps may be used to provide various therapeutic substances such as fluids, insulin, heart rate and blood pressure regulating medications, anti-anxiety drugs, various antagonists and the like. In all embodiments, the patient's reaction to these drugs and substances is monitored via the brain monitoring system, which includes the electrode array, the device and the display device described above, which further could be integrated in a single system, potentially implantable. Such a system can enable the use of Total Intravenous Anesthesia (TIVA); or the use of other patient management therapies (e.g. fluid management, intravenous sedation, diabetes management, epilepsy management, pain management, etc.); or the delivery of other therapeutics such as electric shocks and signals (e.g., ECT, DBS), mechanical shocks and signals, chemical substances and signals, light signals, sound signals; or the use of brain-computer interface; in situations where it was not safe or possible to use such technique before.

In yet other embodiments, the display device or the device itself can directly integrate an infusion mechanism to deliver 1, 2 or more intravenous drugs. Such system, referred in the following as the Integrated Monitoring and Infusion System (IMIS), may optionally be designed and constructed to be small, lightweight, and easily portable without providing cumbersome bulk or awkwardness to the person carrying it, though may preferably be a typical infusion system used in stationary or semi-stationary clinical care applications. The IMIS is also preferably constructed to be rugged and able to withstand forces and shocks attendant to the circumstances in which it is deployed (such as but not limited to battlefield, transport, etc.). In many embodiments, the IMIS comprises at least one syringe infusion pump for automatically adjusting infusion rates of a drug to be administered to the injured subject attached to, embedded in, or otherwise integrated with a portable enclosure or modular system or case. The infusion pump preferably is used to provide and maintain a stable and suitable concentration of at least one drug or substance to the injured subject. In many embodiments, the drug provided is preferably a sedative or anesthetic drug, which the IMIS infuses and monitors to maintain the subject at a stable sedation level with minimal or no human supervision. In many embodiments, alternatively, or in conjunction with the sedation or anesthesia drug, at least one additional infusion pump may be provided for infusion of analgesic medication to provide a stable and suitable level of pain relief or analgesia to the injured subject. In many embodiments, the IMIS is used for sedation and/or pain management purposes to stabilize the patient for en-route care provided while waiting and/or during transport from the point of injury to a location of higher echelon care as well as at all echelons of care including civilian care facilities.

In many embodiments, the IMIS embeds a control algorithm which utilizes input from the brain function monitor, and optionally from a user, to calculate preferred infusion rates of the sedation or anesthetic and/or analgesic drugs. For example, in many embodiments to control algorithm calculates preferred infusion rates based at least in part on a calculated index (e.g., $WAV_{CNS}$) in combination with user inputted data specific to the subject (e.g., weight, height, age, sec, etc.). Preferably, the algorithm performs these calculations substantially in real-time to provide the necessary modifications to the drug infusion rates immediately. In some embodiments the IMIS embeds a control algorithm which utilizes input from the brain function monitor to calculate preferred infusion rates of other therapeutic drugs and substances for patient management (e.g., fluids, insulin, heart rate and blood pressure regulating medications, anti-anxiety drugs, various antagonists and the like), or to control the delivery of other patient management and therapy solutions that were previously mentioned and that not necessarily utilize only infusion but by other avenues including but not limited to gaseous administration and absorption, and utilizing other therapeutic signals and methods (electrical, mechanical, etc.).

The IMIS device may be operated manually or in a semi-closed loop or closed-loop manner. In one preferred embodiment, the IMIS and the associated electrode array are used in the field, on injured subjects, to deliver and maintain a proper level of sedation and analgesia, or other therapeutic substances and methods, while waiting for medical evacuation. In other embodiments, the IMIS can be used in medical evacuation vehicles, for en-route care, to control the level of stress and pain of the patient, or to provide other substances and therapies (e.g., management of fluids, insulin, heart rate and blood pressure regulating medications, anti-anxiety drugs, various antagonists, as well as electrical, mechanical, sound, light and the like therapeutic signals) and keep him or her safe or comfortable. In yet another preferred embodiment, the IMIS is used in the emergency room or other clinical setting and the like in higher echelons of care facilities, to provide sedation or anesthesia or other therapies for patient management. In yet another preferred embodiment, the IMIS is used in the peri-operative environment to provide sedation or anesthesia or other patient management therapies to the patient. Finally, in yet other embodiments, the IMIS can be used in Intensive Care Units (ICUs), to provide sedation or other patient management therapies to the patient and help through his or her recovery process.

The brain function monitor, IMIS, the combination thereof, and the methods for using these systems are preferably designed to be applicable for in-the-field uses as well as stationary, semi-stationary or traditional care environments. In-the-field is meant to be any application, setting, location or circumstance where the subject is injured and does not have immediate, ready access to sophisticated, formal medical care settings. By way of example, and not meant to limit the applications of the present invention, the in-field portable device and methods described herein can be used in battlefield, professional/recreational/amateur sports, or other entertainment (such as concert) venues, or may be utilized by first responders, medical transport and/or evacuation, security, police, or the like in emergency or other injury situations. In other words, the present invention's device(s) and methods are contemplated to be used for many injuries even those with a sudden onset, in order to provide monitoring, assessment, diagnosis, anesthesia, sedation, and/or pain management until the injured subject can be transported to an end care location of upper echelon medical care with equipment that would supplant this portable, disposable device and the methods for its use. Yet, it should be noted that the device discussed in the present invention can also be designed and used in all clinical environments and echelons of care where the patient is stationary or semi-stationary in location. As such the devices and systems of the present invention should at least be portable in the sense that they can be moved readily along with or separate from the subject, for example between rooms or departments of a critical or stationary care facility.

One embodiment of the present invention includes system for controlling anesthesia or sedation of a subject, the system comprising: a physiological signal sensor adapted to acquire a physiological signal from a subject; an infusion pump with a non-concentric pumping mechanism, a tubing entry point and a tubing exit point, the pump adapted to administer anesthetic or sedative to the subject; and a controller adapted to control the infusion pump and administration of the anesthetic or sedative, the controller comprising a processor adapted for receiving the physiological signal from the physiological signal sensor and further comprising an algorithm adapted to perform real-time quantitative monitoring of the physiological signal, wherein the infusion pump is adapted to progressively decrease occlusion at or near the tubing exit point and to reduce flow pulsation.

Another embodiment of the present invention includes system for controlling anesthesia or sedation of a subject, the system comprising: a physiological signal sensor adapted to acquire a physiological signal from a subject; an infusion pump with a non-concentric pumping mechanism, a tubing entry point and a tubing exit point, the pump adapted to administer anesthetic or sedative to the subject; and a controller adapted to control the infusion pump and administration of the anesthetic or sedative, the controller comprising a processor adapted for receiving the physiological signal from the physiological signal sensor and further comprising an algorithm adapted to perform real-time quantitative monitoring of the physiological signal, wherein the infusion pump is adapted to increase occlusion at or near the tubing entry point and progressively decrease occlusion at or near the tubing exit point and to reduce flow pulsation.

Yet another embodiment of the present invention includes a system for controlling anesthesia or sedation of a subject, the system comprising: a physiological signal sensor adapted to acquire a physiological signal from a subject; an infusion pump with a non-concentric pumping mechanism comprising a casing and an epicyclic gear each having a center and being aligned eccentrically such that the casing center is offset as compared to the center of the epicyclic gear, a tubing entry point and a tubing exit point, the pump adapted to administer anesthetic or sedative to the subject; and a controller adapted to control the infusion pump and administration of the anesthetic or sedative, the controller comprising a processor adapted for receiving the physiological signal from the physiological signal sensor and further comprising an algorithm adapted to perform real-time quantitative monitoring of the physiological signal, wherein the infusion pump is adapted to progressively decrease occlusion at or near the tubing exit point and to reduce flow pulsation.

Still another embodiment of the present invention includes a system for controlling anesthesia or sedation of a subject, the system comprising: a physiological signal sensor adapted to acquire a physiological signal from a subject; an infusion pump with a non-concentric pumping mechanism comprising a casing and an epicyclic gear each having a center and being aligned eccentrically such that the casing center is offset as compared to the center of the epicyclic gear, a tubing entry point and a tubing exit point, the pump adapted to administer anesthetic or sedative to the subject; and a controller adapted to control the infusion pump and administration of the anesthetic or sedative, the controller comprising a processor adapted for receiving the physiological signal from the physiological signal sensor and further comprising an algorithm adapted to perform real-time quantitative monitoring of the physiological signal, wherein the infusion pump is adapted to progressively increase occlusion at or near the tubing entry point and progressively decrease occlusion at or near the tubing exit point and to reduce flow pulsation.

Even another embodiment of the present invention includes a system for controlling anesthesia or sedation of a subject, the system comprising: a physiological signal sensor adapted to acquire a physiological signal from a subject; an infusion pump with a non-concentric pumping mechanism comprising a casing and an epicyclic gear each having a center and being aligned geometrically such that the casing has a geometry that is divided into 360 segments and each segment has a percentage occlusion assigned to it, and each percentage occlusion correlates to a specific radius, a tubing entry point and a tubing exit point, the pump adapted to administer anesthetic or sedative to the subject; and a controller adapted to control the infusion pump and administration of the anesthetic or sedative, the controller comprising a processor adapted for receiving the physiological signal from the physiological signal sensor and further comprising an algorithm adapted to perform real-time quantitative monitoring of the physiological signal, wherein the infusion pump is adapted to progressively increase occlusion at or near the tubing entry point and progressively decrease occlusion at or near the tubing exit point and to reduce flow pulsation.

Still yet another embodiment of the present invention includes a peristaltic infusion pump system for delivering intravenous drugs and fluids to a subject, said system comprising: an administration set integrating a cartridge comprising an epicyclic gear mechanism comprising a sun gear, at least two planet gears connected to a roller element, and at least one annular gear, the cartridge further comprising a pumping chamber having an entry opening, an exit opening, and a tubing groove against which the tubing is being occluded by the passage of the roller element, and a pump head module onto which the cartridge is inserted, wherein the pumping chamber groove geometry is such that the distance between the roller and the groove wall is adapted to reduce flow pulsation.

Yet even another embodiment of the present invention includes a peristaltic infusion pump system for delivering intravenous drugs and fluids to a subject, said system comprising: an administration set integrating a cartridge comprising an epicyclic gear mechanism comprising a sun gear, at least two planet gears connected to a roller element, and at least one annular gear, the cartridge further comprising a pumping chamber having an entry opening, an exit opening, and a tubing groove against which the tubing is being occluded by the passage of the roller element, and a locator ring adapted to interface with a corresponding ridge in the pump head module and to guide insertion of the administration set into the pump head module and onto a drive shaft of the pump head module and lock the administration set in the x- and y-axes, and to allow the administration set to be rotated to lock the administration set into the pump head module in the z-axis via the end of the administration set being rotated into a cavity adapted to house an end of the administration set; and a pump head module onto which the cartridge is inserted, wherein the pumping chamber groove geometry is such that the distance between the roller and the groove wall is adapted to reduce flow pulsation.

Even still another embodiment of the present invention includes a rotary peristaltic infusion pump for delivering intravenous drugs and fluids to a subject, said system comprising: an administration set integrating a cartridge comprising at least two rollers and a pumping chamber having an entry opening, an exit opening, and a tubing groove against which tubing is being occluded by the passage of the roller elements, and where the pumping chamber groove geometry is such that the distance between the roller and the groove wall is adapted to reduce flow pulsation; and a pump head module onto which the cartridge is inserted.

Yet still another embodiment of the present invention includes a rotary peristaltic infusion pump for delivering intravenous drugs and fluids to a subject, said system comprising: an administration set integrating a cartridge comprising at least two rollers and a pumping chamber having an entry opening, an exit opening, and a tubing groove against which a soft tubing is being occluded by the passage of the roller elements, a pressure pin pressed against the downstream tubing after the exit opening, and a pump head module onto which the cartridge is inserted, and where a force sensor placed directly above the pressure pin to measure the force actuated by the pressure inside the soft tubing.

Still even another embodiment of the present invention includes a peristaltic infusion pump for delivering intravenous drugs and fluids to a subject, said system comprising: an administration set integrating a cartridge comprising of: an epicylcic gear mechanism, itself comprising of: a sun gear, at least two planet gears connected to a roller element, and at least one annular gear; a pumping chamber having an entry opening, an exit opening, and a tubing groove against which the tubing is being occluded by the passage of the roller, and where the pumping chamber groove geometry is such that the distance between the roller and the groove wall is adapted to reduce flow pulsation; a pump head module onto which the cartridge is inserted.

Other embodiments similar to those listed above may optionally have one or more of the following features: a display weight of less than 4 ounces; the display showing either or both of raw EEG data and processed data about patient brain state; manual enablement/disablement of automated drug administration; measurement of fronto-temporal cortical activity solely to determine whether drugs are needed; built-in infusion and monitoring control algorithms (as discussed later in this application); adaptive monitoring features that provide for use to reduce the risk of sedative overdose in patients with high blood loss; the monitoring system being disposable in its entirety; a paper battery suitable for providing adequate power for the application over adequate measurement/analysis times of at least 2, and preferably 3, and more preferably 4 hours; a display the size of a credit card; a memory to store the signal(s) for analysis later; the capability to automatically detect seizure, suppression, or unconsciousness; the display being capable of displaying indices, warnings, or other messages for the user; portable and ruggedized construction permitting use on the battlefield, at a sporting event, by emergency first responders, and at schools and workplaces; a battery integrated into display such that the display can be traded off and used for later data analysis, while permitting continued monitoring by swapping out with a new display; and an internal memory and USB interface built into the display permitting the display to be plugged into a computer for easy and fast data transfer, reprogramming, software or firmware updates, etc.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

Various embodiments of the present invention may gain the benefit of many existing systems, methods and devices, whose issued patents or pending patent applications are hereby incorporated by reference, including: systems and methods for the detection of seizures and other ictal activity (U.S. Pat. No. 8,538,512; U.S. patent application Ser. No. 13/731,315); various varieties of electrodes and sensors (e.g., U.S. Pat. No. 8,515,522; U.S. patent application Ser. No. 13/899,632); systems and methods for acquiring biosignals in the presence of high-frequency interference (U.S. Pat. Nos. 8,108,039; 9,037,225); systems and methods for detecting burst suppression of physiological signals (U.S. Pat. No. 8,108,039; U.S. patent application Ser. No. 13/216,755); and systems and methods for denoising large-amplitude artifacts in electrograms using time frequency transforms (U.S. patent application Ser. No. 10/968,348), as well as additional issued patents, which are also hereby incorporated by reference, including U.S. Pat. No. 7,603,168 disclosing closed loop systems and processes, U.S. Pat. No. 7,672,717 disclosing artifact detection, and U.S. Pat. No. 7,373,198 disclosing quantification indexes for cortical activity.

It is to be understood that both the foregoing general description and the following detailed description are merely exemplary of the invention, and are intended to provide an overview or framework for understanding the nature and character of the invention as it is claimed. It is understood that many other embodiments of the invention are not directly set forth in this application but are none the less understood to be incorporated by this application. The accompanying drawings are included to provide a further understanding of the invention, and are incorporated in and constitute a part of this specification. The drawings illustrate various embodiments of the invention and together with the description serve to explain the principles and operation of the many embodiments of this invention.

BRIEF DESCRIPTION OF THE DRAWINGS

FIGS. 3A-D. Diagram depicting various views of an administration set or cartridge comprising pumping mechanics, including: A) cross-section view from top or front with planet gears; B) bottom or back view; C) perspective view of the pump head module showing the pumping mechanics; and D) cross-section view from bottom or back with rollers.

DETAILED DESCRIPTION OF THE PREFERRED EMBODIMENTS

Figure 1:
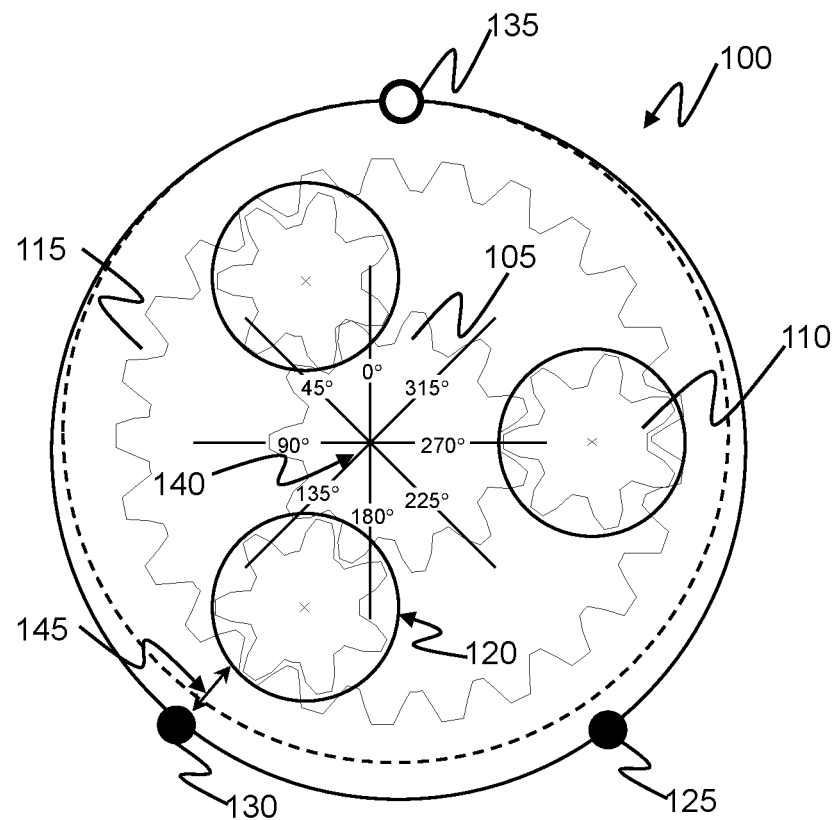
FIG. 1. Diagram depicting an eccentric peristaltic pump gear mechanism.

The present invention relates to the monitoring and processing of signals, and particularly to the monitoring and processing of electrophysiological signals. More particularly, the present invention relates to processing electroencephalographic (EEG) signals to monitor brain function. Further still, the present invention relates to a system for controlling sedation or anesthesia for transportation or evacuation of the injured as well as closed-loop sedation or anesthesia at all echelons of care, including civilian and critical care facilities.

For the present invention, the subject whose EEG signal is being measured can be any type of animal, preferably a mammal, most preferably a human. Also, caregiver and clinician are understood to include not only those skilled in the use of EEG equipment and methodologies, such as doctors, physicians, anesthesiologists, EEG technologists, emergency response personnel, nurses, and the like. The device and methods are designed to be used and performed, respectively, largely by untrained or minimally trained personnel, until the injured subject may be transported to a clinician as described above for more acute and skilled care in proper facilities or locations.

The various embodiments of the present invention are preferably one or more of portable, ruggedized, disposable, and capable of rapid application and use. By "portable" it is meant that a single embodiment is light enough in weight and compact enough in size to be carried in a small handheld and hand-carried case that may be carried easily by a single person and applied to a subject or patient without impeding the subject's easy and safe transport. Preferably, this means that the subject is completely untethered, except, in some embodiments, to a small monitor and/or therapy device which can be attached to the subject, the subject's clothing or gear, or the subject's gurney, stretcher, or bed and easily moved along with the subject. Preferably, the entire system weighs less than 75 lbs. More preferably, the entire system weighs less than 60 lbs. Still more preferably, the entire system weighs less than 50 lbs. Yet more preferably, the entire system weighs less than 40 lbs. Even more preferably, the entire system weighs less than 25 lbs. Still more preferably, the entire system weighs less than 20 lbs. Yet more preferably, the entire system weighs less than 15 lbs. Even more preferably, the entire system weighs less than 10 lbs. By "ruggedized" it is meant that the embodiment has features that harden it to mechanical and electrical shocks and dust/fluid ingress, etc., as described elsewhere in this application which permit the embodiment to be transported and used in emergency settings. "Disposable" is defined by a number of factors as discussed elsewhere in this application. "Rapid application and use" means that the system or apparatus embodiment can be taken from a storage or transportation configuration, applied to a subject or patient, and used for measurement, monitoring, analysis and/or therapy in less than ten minutes. More preferably, application can be performed in less than one minute. More preferably, application can be performed in less than thirty seconds. Still more preferably, application can be performed in less than ten seconds. More preferably still, application can be performed in less than five seconds. Such rapid applications can be realized by providing a monitor embodiment as a simple adhesive patch that is peeled from a backing and applied to a patient or subject's forehead, whereupon the monitor embodiment automatically activates, self-calibrates, and begins measurement, monitoring, analysis, and/or therapy.

Various embodiments of the systems and devices of the present invention include one or more of the following elements and variations thereof. These elements include, but are not limited to, a physiological signal sensor adapted to acquire a physiological signal from a subject; an infusion pump with a non-concentric pumping mechanism comprising a casing and an epicyclic gear, a tubing entry point and a tubing exit point, the pump adapted to administer anesthetic or sedative to the subject; and a controller adapted to control the infusion pump and administration of the anesthetic or sedative, the controller comprising a processor adapted for receiving the physiological signal from the physiological signal sensor and further comprising an algorithm adapted to perform real-time quantitative monitoring of the physiological signal, wherein the infusion pump is adapted to progressively increase occlusion at or near the tubing entry point and progressively decrease occlusion at or near the tubing exit point and to reduce flow pulsation, an administration set integrating a cartridge comprising an epicyclic gear mechanism comprising a sun gear, at least two planet gears connected to a roller element, and at least one annular gear, the cartridge further comprising a pumping chamber having an entry opening, an exit opening, and a tubing groove against which the tubing is being occluded by the passage of the roller element, and a locator ring adapted to interface with a corresponding ridge in the pump head module and to guide insertion of the administration set into the pump head module and onto a drive shaft of the pump head module and lock the administration set in the x- and y-axes, and to allow the administration set to be rotated to lock the administration set into the pump head module in the z-axis via the end of the administration set being rotated into a cavity adapted to house an end of the administration set; and a pump head module onto which the cartridge is inserted, wherein the pumping chamber groove geometry is such that the distance between the roller and the groove wall is adapted to reduce flow pulsation.

The casing of the administration set/cartridge may further preferably comprise one or more alarm indicators. The alarm indicators serve to provide visual messages to a user of the system. One preferred form of alarm indicators includes light indicators and corresponding channels or light pipes in the casing that allow light to be transmitted and to be visual from large viewing angles. The light sources integrated into the administration set/cartridge may be any form of light emitting device known in the art, but are preferably LEDs. The lights further preferably are capable of emitting different colors of light which may correspond to various statuses of the device and system. The channels or light pipes preferably are adapted so that the lights may be visible from virtually any viewing angle with respect to the device. The light source(s) are preferably situated within the casing of the administration set/cartridge, and the channels or light pipes constitute grooves in the casing that extend from the light source to the front surface of the casing. Preferably, the alarm indicators have at least 90° vertical visibility. More preferably, the alarm indicators have at least 100° vertical visibility. Still more preferably, the alarm indicators have at least 110° vertical visibility. Yet more preferably, the alarm indicators have at least 120° vertical visibility. Even more preferably, the alarm indicators have at least 130° vertical visibility. Still yet more preferably, the alarm indicators have at least 140° vertical visibility. Even still more preferably, the alarm indicators have at least 150° vertical visibility. Yet still more preferably, the alarm indicators have at least 160° vertical visibility. Still even more preferably, the alarm indicators have at least 170° vertical visibility. Most preferably, the alarm indicators have at least 180° vertical visibility. Additionally, preferably, the alarm indicators have at least 180° horizontal visibility. More preferably, the alarm indicators have at least 200° horizontal visibility. Yet more preferably, the alarm indicators have at least 220° horizontal visibility. Still more preferably, the alarm indicators have at least 240° horizontal visibility. Even more preferably, the alarm indicators have at least 260° horizontal visibility. Still yet more preferably, the alarm indicators have at least 280° horizontal visibility. Even still more preferably, the alarm indicators have at least 300° horizontal visibility. Yet still more preferably, the alarm indicators have at least 320° horizontal visibility. Still even more preferably, the alarm indicators have at least 340° horizontal visibility. Most preferably, the alarm indicators have at least 360° horizontal visibility. Preferably, at least one light pipes or channels are used to transmit light corresponding to alarms, signals or messages. More preferably, at least two light pipes or channels are used to transmit light corresponding to alarms, signals or messages. Yet more preferably, at least three light pipes or channels used to transmit light corresponding to alarms, signals or messages. Still more preferably, at least four light pipes or channels used to transmit light corresponding to alarms, signals or messages. Even more preferably, at least five light pipes or channels used to transmit light corresponding to alarms, signals or messages. Still yet more preferably, at least six light pipes or channels used to transmit light corresponding to alarms, signals or messages. Yet even more preferably, at least seven light pipes or channels used to transmit light corresponding to alarms, signals or messages. Even still more preferably, at least eight light pipes or channels used to transmit light corresponding to alarms, signals or messages. Alternatively, instead of individual light pipes or channels corresponding to individual light sources, a single channel can be used that extends 360° around the pumping chamber which conveys messages from either multiple individual light sources or a common light source. In order to further facilitate the visibility of the alarm indicators via the channels or light pipes, the side walls of the casing of the administration set/cartridge may preferably be tapered, creating a smaller front surface of the casing compared to the base and allowing for more light to be visible from larger viewing angles. Still further, the casing may be composed of a type of material that allows for the light to be visible to some degree through the material, i.e., the material may be transparent or opaque but capable of partially transmitting light through the material or becoming illuminated by the light being emitted by the alarm indicator(s). The alarm indicators, aside from being capable of emitting various colors of light, may further be capable of emitting light in different intensities or patterns to further distinguish between various statuses of the system. The alarm indicators may be used to communicate various status messages to a user, for example, high occlusion percentage, low occlusion percentage, high or low flow rate of the fluid or medication being delivered, loss of power, or numerous other issues or statuses that may need to be conveyed to a user.

Many embodiments of the present invention include a peristaltic pump. The peristaltic pump of the present invention includes numerous innovations that address shortcomings of such pumps presently known in the art. There are various types of peristaltic pumps presently known each with particular advantages and disadvantages as well as particular applications. Preferably, the present invention utilizes a rotary peristaltic pump where a servo/controlled stepper motor drive is coupled to a set of rollers compressing a flexible tube. Rotary peristaltic are positive displacement pumps, where the fluid to be pumped is contained within a flexible tube fitted inside a circular casing. The rotor is fitted with a number of rollers to its external circumference, and which compress the flexible tube. As the rotor turns, the part of the tube under compression is occluded thus forcing the fluid to move through the tube. Additionally, as the tube opens to its natural state after the passing of the roller, fluid flow is induced to the pump. Typically, there will be two or more rollers occluding the tube, trapping between them a body of fluid. This is a very simple and compact mechanism. Even if the tubing is empty of liquid, the rotational movement of the rollers will create a negative pressure in the pump inlet, which will force any liquid in a reservoir attached to the inlet to flow towards the pump. The roller assembly and casing are referred to as the 'pump head'. Typically, the pump head is part of the pump itself. It may be replaced after a long utilization. In this case, the pump head allows users to open the casing to replace the tubing. Tubing is typically made of silicone and needs to be replaced frequently, between uses. A problem of such mechanism is that the tubing, if removed from its casing, will not have any of its length occluded by the rollers. As such, depending on the respective position of the drug reservoir and the patient, free-flow will occur (i.e., the drug in the reservoir infuses directly in the patient at an uncontrolled rate, or the patient bleeds inside the drug reservoir, at an uncontrolled rate). Free-flow can be very dangerous to the patient and needs to be absolutely prevented. This is typically done by having the human operator clamp the tube anywhere on its length. Another problem is the tubing itself. By allowing a user to change the tube inside the casing of the pump, multiple user-based errors can be made (e.g., wrong positioning, wrong tube selection, etc.), which may prevent the proper operation of the system, and result in over- or under-dosing and other safety issues. In order to address these issues, some embodiments of the present invention may make the pump head itself fully disposable and single use. One advantage of this solution is the inherent free-flow prevention; since the tube cannot be removed from the pump head (at least one roller always occludes the tube). Another advantage is the better control over wear-and-tear of the pumping mechanism. By limiting to a finite time, e.g., 24 hours, the life of the pump head, we are assured of its precision and reliability during this time frame. This also makes longevity testing easier.

In light of this, the present invention utilizes an administration set that can be disposable and which can be inserted into the peristaltic pump. This administration set comprises a cartridge that contains all of the pumping mechanisms required to provide the desired movement of fluid or medication. Preferably, the administration set and/or cartridge is a modular component that can be easily inserted into and removed from the peristaltic pump. Preferably, the administration set/cartridge comprises a series of features to facilitate simple installation and removal, including a locator ring and twist-and-lock capability. The locator ring is preferably a groove located on the back side of the administration set/cartridge that corresponds to a ridge or other similar raised feature on the interior of the pump itself. The locator ring is designed such that the administration set/cartridge can be placed into the pump and situated so that the raised feature of the pump fits into the locator ring. This effectively guides the administration set/cartridge to be placed in the proper location and prevents movement in the x- and y-axes. The administration set/cartridge can then be rotated along the locator ring and raised feature interlocked together until a locking tab or protrusion on the administration set/cartridge snaps or locks into place in a notch or cavity also located in the pump module, or in a cradle within the pump module that mirrors the shape of the administration set/cartridge. Once the administration set/cartridge has been rotated into its locked position, the locator ring maintains the position in the x- and y-axes and the locking tab or protrusion in the notch or cavity of the pump or cradle within the pump locks the administration set/cartridge in the z-axis. Thus, with one hand and no tools required, an operator can easily insert and lock the administration set/cartridge into place in the pump module, and conversely can remove it just as easily. Additional locking tabs or protrusions and corresponding notches or cavities may be included at various locations around the administration set/cartridge in order to provide additional locking points to keep the administration set/cartridge in place in the z-axis. Another optional feature includes an O-ring gasket that may be inserted into the locator ring. Such a gasket helps to prevent ingress of fluids, dust or other contaminants that may enter the administration set/cartridge and potentially damage the gear system or internal sensors, or the pump mechanics themselves, such as the motor or driver of the pump. The administration set/cartridge also further preferably comprises a transparent or semi-transparent from surface or cover which allows the internal gear system to be visible to a user. This provides the user with easy and rapid visual access to ensure the pump system is working properly.

The administration set/cartridge comprises the mechanics for causing the pump to operate to advance and deliver the fluids or medication to the subject. An epicyclic gear comprising a sun gear (central gear) which through the cartridge connects to the driver of the pump module which controls the rotation of the gears within the administration set/cartridge, at least two planet gears and an annular gear. The planet gears preferably each comprise a roller either attached to each planet gear or integrated onto each planet gear. As the pump module driver causes the sun gear to rotate, the sun gear, by virtue of teeth or grooves on its outer edge and corresponding to interlocking teeth or grooves on the outer edges of the planet gears, to rotate in turn. This rotation causes the rollers to move around axis of the sun gear and rotate with the gear system. An annular gear is further disposed such that the planet gear fit between the sun gear and the annular gear, each interlocking by teeth or grooves one the outer edges of the sun and planet gears and on the inner edge of the annular gear. Thus, the entire gear system remains stable and locked into place during rotation. To further facilitate the stability of the gear system and rollers or roller elements, a retaining wall may optionally be utilized within the casing of the administration set/cartridge which provides a surface for the rollers or roller elements to move long when travelling between the exit opening and the entry opening. This retaining wall prevents the remaining roller(s) or roller element(s) that are within the pumping area from pushing the roller(s) or rolling element(s) that are outside the pumping area to far out of place, or from allowing the any portion of the gear system to shift.

Surrounding the epicyclic gear arrangement is a pumping chamber. The pumping chamber comprises the space where the tubing rests in the pump and comes into contact with the rollers attached to or integrated onto the epicyclic gear. The pumping chamber further an entry opening and an exit opening which constitute apertures in the administration set/cartridge into which the tubing fits. Still further, the pumping chamber comprises a tubing groove which allows the tubing to be situated within the pumping chamber along the length of an interior wall of the administration set/cartridge casing from the entry opening to the exit opening. When fully assembled, the administration set/cartridge causes the rollers or roller elements to come into contact with the tubing situated in the tubing groove and to pinch the tubing, at least partially, between the rollers or roller elements and the wall of the tubing groove, thereby causing occlusion of the tubing. Thus, as the epicyclic gear rotates, the rollers or roller elements pinch the tubing and rotate around the pumping chamber causing the fluids or medications to advance through the tubing from the entry opening to the exit opening. The present invention leverages this pumping mechanism to reduce or eliminate flow pulsation anomalies by progressively decreasing the amount of occlusion of the tubing at or near the exit opening.

Another feature of the present invention is a strain relief path or channel that optionally is integrated into the casing of the administration set/cartridge. Pressure applied to the tubing, such as pulling, tugging or snagging of the tubing extending from either end of the administration set/cartridge, can cause damage to the tubing or the system. In embodiments comprising the strain relief path or channel, the casing of the administration set/cartridge comprises an extended tubing groove that extends through a larger portion of the casing and traverses in such a path as to allow for strain relief preventing the tubing from being pulled from the entry and exit openings, or from allowing two different sections of tubing from being pulled apart. Some embodiments may utilize multiple types of tubing, for example a softer, larger diameter tubing inside the pumping chamber with a harder, smaller diameter, kink-resistant tubing traveling from the fluid or medication source to the pump and/or from the pump to the deliver mechanics, such as intravenous needle. One example of such a strain relief path would be a circular indentation in the casing whereby the tubing enters the casing of the administration set/cartridge via the entry opening, is placed in a circular strain relief groove, then enters the tubing groove situated in the pumping chamber then returns to the circular strain relief path before exiting through the exit opening. Such a design provides relief from direct forces that might pull the two types of tubing apart or pull a single tubing out of the pump system by redistributing the force along the strain relief path, thus maintaining a secure system and minimizing risk of having tubing pulled out and the fluids or medications prevented from reaching the subject. Although the strain relief path described is circular, alternate shapes or path formations may be used, such as U-shaped or elliptical. Another optional feature of the administration set/cartridge that can help prevent uncoupling of tubing and help reduce strain on the tubing includes a crimping surface integrated into the casing at or near each of the entry and exit openings. The crimping surface may comprise a raised, grooved element on at least one side of the casing in the tubing groove that provides additional contact between the casing and the tubing when the administration set/cartridge is assembled with the tubing in place and provides pressure against the tubing. Preferably, this crimping surface would be located near the entry and exit openings of the administration set/cartridge and provide the additional crimping pressure on a length of tubing corresponding to the coupling between the softer tubing inside the administration set/cartridge and the harder, kink-resistant tubing extending out therefrom.

In order to provide progressive and continuous occlusion release, several pumping geometries may be used for the arrangement of the epicyclic gear system. One such option is to utilize an eccentric pumping mechanism. In such embodiments, the epicyclic gear is offset from the center of the casing of the administration set/cartridge. This design helps to reduce the amount of occlusion as the roller gets closer to the tubing exit. In particular, the occlusion should reach, at most, 0% when the roller reaches the exit point. Because the roller progressively 'opens up' the occlusion, the flow pulsation anomaly averages out over the complete motion of the roller. By way of non-limiting example, as the roller moves from the entry point to the exit point, the tubing first sees an increasing occlusion. At 90°, the occlusion reaches its maximum. In this exemplary design, the maximum occlusion is 20% (i.e., the distance between the casing and the roller is 80% of the total wall thickness of the tubing). Once the roller passes the 0° position, the occlusion starts to decrease progressively. At the exit point, the occlusion is −5%, which means that the tube is no longer occluded. Despite the exemplary values for occlusion utilized above, maximum occlusion may be any value defined by the manufacturer or possibly operator of the system, but must be sufficient to maintain pressure and forward flow of the fluid or medication while preventing backflow. One advantage of this design is the way the tubing is progressively being pinched as the rollers move over the entry point. This provides a smoother transition of entry occlusion, and limits the amount of torque (i.e., force) needed to move the roller, and extends the life of the tubing. Effectively, the eccentric pumping mechanism serves to spread the anomaly over the complete pumping segment (the pumping segment is the last segment of tubing prior to the flow exiting the pumping chamber—this is the segment that actually pushes fluid out of the chamber). In the eccentric mechanism, the occlusion reduces progressively as the roller gets closer to the exit point. In fact, the occlusion becomes negative just prior the exit point (the tube is open at this point). Depending on the eccentric mechanism's design, flow pulsation anomalies may still occur, though still far less severe and far less often than traditional pumps, particularly if the mechanism is design to have the roller or roller element completely release occlusion at the exit opening of the pumping chamber where the roller element is still in contact with the tubing, even if not causing occlusion. In such a design, even though the tubing is not occluded, it is still slightly compressed from the contact of the roller or roller element, and as the roller or roller element clears the exit opening and is no longer in contact with the tube, the tube returns to its original round shape and the pumping volume increases, which slows the flow of the fluids or medications in the tube. Thus, it may be preferable to design the epicyclic gear system and casing of the administration set/cartridge to remove the roller or roller element from any contact with the tubing prior to reaching the exit opening, thus allowing the tube to return to its initial round shape prior to exiting the pumping chamber. Eliminating the spring effect of the tubing expanding back to its original round shape in turn minimizes or eliminates any slowing of the flow of the pumping volume exiting the pumping chamber.

Another option is to use a geometric pumping mechanism whereby the circular geometry of the pumping chamber (including the portion where there is no tubing) into discrete segments and defining each segment in terms to a specific percent occlusion. For example, the circular geometry can be divided into 360 segments, where each segment is defined to provide a specific percentage occlusion. This geometric pumping mechanism is preferably epicentric with the epicyclic gear centered on the center of the case of the administration set/cartridge, though the geometry of the casing does not have to be symmetrical. In such a design, maximum occlusion is typically specified when potentially only one roller or roller element provides occlusion of the tubing. For example, if three planet gears with associated rollers or roller elements are present, there can be a point when only one roller or roller element is providing occlusion and the other two rollers or roller elements are approaching the entry opening and just past the exit opening, respectively. In such example, the maximum occlusion would be defined at the point where the single roller is in contact with the tubing and occluding it. The points of the casing between the exit opening and the entry opening are effectively undefined because there is no tubing there and therefore no occlusion to be considered. BY way of further example, maximum occlusion can be defined as 20%, and this is provided at the point where the single roller is in contact with the tubing, which can be defined as 0°. Occlusion at the entry point where the tubing enters the entry opening and the roller or roller element first comes into contact with the tubing can be defined as 0% and as being at 220°, therefore, as soon as a roller enters the loading segment, which is the first segment of the pumping chamber from the entry opening to the location where one roller reaches as the next roller reaches the entry opening, occlusion is provided. The exit opening could then be defines as being located at 140° and having an occlusion of −30%. In order to achieve the desired release of occlusion and return of the tubing to its original round shape, the point at which the tubing reaches 0% occlusion can be defined as 90°. Thus, the tubing is no longer occlude before the exit opening, and the tubing further reaches its original shape prior to the exit opening, and flow anomalies are minimized or eliminated.

The present invention's ability to minimize or eliminate flow pulsation and related anomalies further provides the system with the benefit of being capable of operating in larger ranges of flow rates. The flow pulsation anomalies address by the present invention typically arise at lower flow rates, and therefore most systems tend to operate only at higher flow rates where these anomalies are not as prevalent. The present invention, however, is capable of operating safely and consistently at both low and high flow rates without the occurrence of such anomalies. Preferably, the system can provide flow rates greater than 200 ml/hr without exhibiting flow pulsation anomalies. More preferably, the system can provide flow rates greater than 180 ml/hr without exhibiting flow pulsation anomalies. Yet more preferably, the system can provide flow rates greater than 160 ml/hr without exhibiting flow pulsation anomalies. Still more preferably, the system can provide flow rates greater than 140 ml/hr without exhibiting flow pulsation anomalies. Even more preferably, the system can provide flow rates greater than 120 ml/hr without exhibiting flow pulsation anomalies. Still yet more preferably, the system can provide flow rates greater than 100 ml/hr without exhibiting flow pulsation anomalies. Yet even more preferably, the system can provide flow rates greater than 80 ml/hr without exhibiting flow pulsation anomalies. Even still more preferably, the system can provide flow rates greater than 60 ml/hr without exhibiting flow pulsation anomalies. Yet still more preferably, the system can provide flow rates greater than 40 ml/hr without exhibiting flow pulsation anomalies. Still even more preferably, the system can provide flow rates greater than 20 ml/hr without exhibiting flow pulsation anomalies. Even yet more preferably, the system can provide flow rates greater than 10 ml/hr without exhibiting flow pulsation anomalies. Most preferably, the system can provide flow rates greater than 0.5 ml/hr without exhibiting flow pulsation anomalies. High flow rates can also cause anomalies to occur, or other anomalies may arise such as failure of system components due to high pressure (e.g., bursting of the tubing, motor stall, release of tube coupling, and the like), but the system preferably is capable of operating at very high flow rates as well without exhibiting flow pulsation or failure anomalies. Preferably, the system can provide flow rates greater than 2000 ml/hr without exhibiting flow pulsation or failure anomalies. More preferably, the system can provide flow rates greater than 2500 ml/hr without exhibiting flow pulsation or failure anomalies. Still more preferably, the system can provide flow rates greater than 3000 ml/hr without exhibiting flow pulsation or failure anomalies. Yet more preferably, the system can provide flow rates greater than 3500 ml/hr without exhibiting flow pulsation or failure anomalies. Even more preferably, the system can provide flow rates greater than 4000 ml/hr without exhibiting flow pulsation or failure anomalies. Still yet more preferably, the system can provide flow rates greater than 4500 ml/hr without exhibiting flow pulsation or failure anomalies. Yet even more preferably, the system can provide flow rates greater than 5000 ml/hr without exhibiting flow pulsation or failure anomalies. Even still more preferably, the system can provide flow rates greater than 5500 ml/hr without exhibiting flow pulsation or failure anomalies. Yet still more preferably, the system can provide flow rates greater than 6000 ml/hr without exhibiting flow pulsation or failure anomalies. Still even more preferably, the system can provide flow rates greater than 6500 ml/hr without exhibiting flow pulsation or failure anomalies. Most preferably, the system can provide flow rates greater than 7000 ml/hr without exhibiting flow pulsation or failure anomalies.

In order to ensure the proper occlusion of the tubing throughout the pumping chamber, many embodiments may include an occlusion detection system. Such occlusion detection systems preferably utilize at least one force sensor located on the tubing, within the pumping chamber or external to the administration set/cartridge. One preferred force sensor is a piezo-electric force sensor that measures pressure as a function of resistance. The sensor comprises two conductive plates which exhibit a known resting impedance between them, and as pressure increases, the impedance between the plates decreases. The variation in the impedance of the sensor plates is directly related to the change in pressure in the tubing. However, other pressure sensors presently known or later developed may be used to detect occlusion as well. Multiple sensor may be used to detect upstream and downstream pressure in order to detect and monitor occlusion both at or near the entry opening and at or near the exit opening. The force sensor(s) may additionally be used to determine proper assembly of the system, for example by the force measurement being used to detect the presence of the administration set or cartridge when it is placed into the pump head module and/or to determine proper placement via location, orientation or the like, of the administration set or cartridge in the pump head module.

Various embodiments of the methods of the present invention include one or more of the following steps, and variations thereof. These steps include, but are not limited to, monitoring a subject with a brain having a left hemisphere and a right hemisphere, by connecting the subject to a brain function monitoring device with at least one electrode lead comprising at least one measurement electrode and at least one reference electrode, the at least one electrode lead comprising at least one EEG electrode, having a signal associated therewith, positioned on a subject's head to monitor activity of the subject's brain, the reference electrode comprising at least one EEG electrode, each electrode providing an EEG signal. Alternatively, monitoring of the subject's brain function can be performed with at least one electrode array comprising a plurality of measurement EEG electrodes and at least one reference electrode, each of the plurality of EEG measurement electrodes having a signal associated therewith.

Similarly, various extended embodiments of the device of the present invention include one or more of the following components, and variations thereof. These elements include, but are not limited to, an electrode array(s), a display device, an anesthetic or sedation infusion and monitoring system, a processor, which may embed signal processing algorithms, and/or a control algorithm(s) for controlling drug infusion, and drug infusion device(s).

All embodiments of the present invention involve acquiring an electroencephalographic (EEG) or functionally equivalent signals from a subject or a patient utilizing a physiological signal sensor. In acquiring EEG signals, electrodes can be placed at various locations on the subject's scalp in order to acquire EEG or brain wave signals. Common locations for the electrodes include frontal (F), temporal (T), parietal (P), anterior (A), central (C) and occipital (O). If the particular embodiment utilizes an array of electrodes, the array may contain electrodes positioned at one or several of these or other locations. Preferably for the present invention, at least one electrode is placed at or near the fronto-temporal region of the subject's brain, on the subject's scalp. Additionally, preferably at least two electrodes are used, one signal electrode and one reference electrode; if further EEG or brain wave signal channels are desired, the number of electrodes required will depend on whether separate reference electrodes are used or, instead, a single reference electrode is used for multiple channels. The step of monitoring brain function includes using at least one sensor, including physiological signal sensors, to measure a subject's brain wave signals over a period of time. The brain wave or EEG signals can be obtained by any method known in the art, or subsequently developed by those skilled in the art to detect these types of signals. Sensors include but are not limited to physiological signal sensors such as electrodes or magnetic sensors. Since brain wave signals are, in general, electrical currents which produce associated magnetic fields, the present invention further anticipates methods of sensing those magnetic fields to acquire brain wave signals similar to those which can be obtained through for example an electrode applied to the subject's scalp.

The electrodes may be affixed to or preferably embedded into a flexible, wearable apparatus which can be applied directly to the injured subject's head, preferably the forehead. Preferably, the wearable apparatus is designed to be flexible, easy to don and doff, and disposable yet still resilient and capable of withstanding forces common in emergency settings. As used in this application, an "emergency setting" is limited to places and events outside of hospitals, clinics, and other places where trained medical professionals are close at hand. Exemplary emergency settings include battlefields; settings of vehicle or construction accidents; sites of mass casualty, terrorist attack, or natural or industrial disaster; schools; sports fields and arenas; shopping areas, pedestrian areas, and other places generally open to the public; workplaces, homes, and residences, and the like. A staffed and equipped emergency room is not an "emergency setting." Forces common in emergency settings include those previously mentioned as well as those associated with roughly ported or dropped—accelerations and shocks uncommon in hospital and emergency room settings and which would damage or destroy equipment designed for use in a hospital. However, it is to be noted that the current invention is not limited to use in emergency settings only. The apparatus may be secured about the subject's head by means commonly known to those in the art, including, but not limited to, a cap or other garment completely encompassing the subject's head, a strap that is secured by compression or elastic means, or may utilize common fastening methods such as hook-and-loop, belt-type, snap connectors, or the like. Additionally, or in conjunction with one of the above means, an adhesive layer may be used in conjunction with a wearable apparatus to further ensure a stable, secure placement of the electrode lead or array. In a preferred embodiment, the flexible apparatus is a small patch-type garment comprising an adhesive layer which, when applied to the injured subject's forehead, is capable of maintaining a secure placement with minimal shifting, drift, or other movement of the apparatus, for the entire length of time necessary for monitoring. The adhesive layer is also preferably capable of providing a secure, stable attachment to the subject in the presence of dirt, sweat, and other detritus which may be covering the subject's skin during application, without the need for washing, cleaning or otherwise preparing the area of application. Preferably, in preferred embodiments where the electrode array or sensing system is affixed to or embedded in a patch-type garment, the patch is small and easily applied. Preferably, the surface area of the sensing system and/or patch, including electrode array(s) is less than 10 square inches. More preferably, the surface area of the sensing system and/or patch is less than 8 square inches. Even more preferably, the surface area of the sensing system and/or patch is less than 6 square inches. Still more preferably, the surface area of the sensing system and/or patch is less than 4 square inches. Yet more preferably, the surface area of the sensing system and/or patch is less than 2 square inches. Other similar methods of acquiring physiological signals may be used in the present invention which are known to those skilled in the art for acquiring signals such as electrocardiography (ECG), electrical impedance tomography (EIT), electromyography (EMG) and electro-oculography (EOG).

In order to obtain a good EEG or brain wave signal it is desirable to have low impedances for the electrodes. Typical EEG electrodes connections may have impedance in the range of from 5 to 10 kilo-ohms. It is, in general, desirable to reduce such impedance levels to below 2 kilo-ohms. Therefore a conductive paste or gel may be applied to the electrode to create a connection with impedance below 2 kilo-ohms. Alternatively, the subject's skin may be mechanically abraded, the electrode may be amplified using active circuitry, or a micro-penetrating dry electrode may be used. Dry physiological recording electrodes of the type described in U.S. Pat. No. 6,785,569 can be used. U.S. Pat. No. 6,785,569 is incorporated by reference. Dry electrodes provide the advantage that there is no gel to dry out, no skin to abrade or clean, and that the electrode can be applied in hairy, sweaty, and/or dirty areas such as the scalp, particularly for in-the-field applications.

It is also contemplated that the electrodes may be nothing more than electrode pads consisting of a thin conductive coating (e.g., a coating of silver or other metal) printed onto the underside of a flexible substrate. In such an embodiment, the flexible substrate preferably has flexible printed circuit board (PCB) traces embedded in it to carry signals acquired by the electrodes or electrode pads to processing electronics. Although "dry" in the sense that these simple electrodes have no electrode gel, such electrodes are to be distinguished from the dry electrodes mentioned above, and are not referred to herein as dry electrodes.

Almost all embodiments of the present invention include a display. Preferably, the display provides a touch-screen interface for the caregiver to interact with the system, although other control means such as analog buttons, or a combination of screen output and analog or digital controls may be used. In some embodiments, the display may simply integrate light-emitting diodes (LEDs) as a means of displaying visual information to the user. In other embodiments, the display may be more complicated, such as a touch screen, which also provides a direct user interface. Also, a processor may be integrated in the display unit to process the EEG signals. This processor can be based on a reduced instruction set computing (RISC) microprocessor, or a digital signal processor (DSP). Preferably, the processor is a microprocessor sufficiently miniaturized to fit into the small device or display and provides little or no bulk or weight to the device. Further, the processor embeds algorithm(s) for making particular determinations, e.g., presence of seizure activity, EEG slowing, low cortical activity level, presence of EEG amplitude loss or cortical suppression. In a particular context-of-use, such as a far forward deployment, a trigger in any of these endpoints may point to the presence of abnormal function or injury, such as TBI. In particular, the determinations are made based on at least one of several algorithms coinciding with the above described methods and steps, including, but not limited to, seizure detection, cortical suppression detection, EEG slowing detection, cortical activity level measurement, and the like. The algorithms can be used on a single EEG channel, two channels, or more, as needed. Processed information from two or more channels may be combined to improve the determination of the presence or absence of abnormal activity or injury. Other algorithms may be provided, including, but not limited to, those for providing measures such as spectral edge frequency (SEF) or the median edge frequency (MEF), or other methods based on entropy and/or bispectral analysis.

In many embodiments, the display also optionally contains internal memory for storage of acquired and/or processed EEG signals, calculated data (e.g., EEG events such as seizure or suppression, indices, alerts, and the like), and/or logistical data (e.g., time, location, GPS coordinates, and the like). The internal memory may consist of a removable flash memory card such as an SD, miniSD, microSD, MMC, CompactFlash, or the like. Alternatively, or in addition, the display may contain an internal, non-removable memory for such storage. In such embodiments, the non-removable memory may be read by connecting the display to another device by means of a cable, or by virtue of an incorporated USB-type attachment that may fold out of the display to be inserted directly into another device. Some embodiments may provide both non-removable and removable memory to provide redundancy in the data storage in the even that one of the memory components is destroyed, damaged or lost. Data from the memory may in some embodiments be transmitted by wired or wireless transfer using any of the protocols described in this application or known to those skilled in the art.

The display further optionally comprises an internal power source. Such internal power source furthers the ease and simplicity of use of the device by removing the need for power cables or cords, as well as the external power source. This also increases the portability of the device. Such internal power source may be a battery of any type known to those in the art that is suitable for the type of applications envisioned for the device, and that contain sufficient life to power the device from deployment until the subject is delivered to a location of higher echelon care and can be monitored by more permanent, robust equipment and caregivers. In addition to a battery, the display may incorporate a source of renewable or regenerative power, such as solar power to maintain the life of the display.

In some embodiments of the present invention, the physiological signal monitor includes the electrodes, display and signal acquisition electronics constitute the physiological signal monitoring component, and may further include an automatic, continuous electrode impedance checking ability. Traditional impedance checking techniques require the monitoring system to halt biosignal acquisition and monitoring in order to check and measure the impedance of a given electrode. However, continuous impedance checking, in the context of the present invention, means that impedance can be measured simultaneously with continued, uninterrupted monitoring and acquisition of the desired biosignal. In other words, the acquisition function of an electrode does not need to be halted in order to check the impedance of any given electrode. In order to continuously check electrode impedance, such embodiments require an alternating current source generator that is capable of progressively increasing and decreasing electrical current into the individual measurement electrodes. Preferably, the current supplied to the measurement electrodes is supplied at a known amplitude and frequency. Also preferably, the frequency of the supplied current is outside of the biological frequency of the physiological signal being monitored (herein referred to as the bio-band). Supplying the current outside the biological frequency for the signal from the electrode being measured prevents interference with the diagnostic signal— preventing perturbation of the measured physiological signal. For example, the typical biological frequency (bio-band) of EEG signals is from about 0.5 Hz to about 70 Hz, but can expand to between 0.125 Hz to about 120 Hz. Meanwhile, the typical bio-band for EMG signals ranges from about 30 Hz up into the kilohertz range. The maximum level of the impedance measurement current supplied further depends on the electrical instrumentation utilized as well as legal limits set with regard to patient care, depending on the application. The supplied current must be within the limits of the instrumentation so as not to overload the amplifiers and cause the system to fail. Also, regulations limit currents supplied to the human body to levels below 10 microamps.

Once the electrical current being supplied to the first measurement electrode has reached the predetermined maximum stabilized current, the voltage resulting from the supplied current is measured across the system. The voltage and current values are known to the system and are used to calculate an electrical impedance of the first measurement electrode. Preferably, this voltage measurement and impedance calculation is carried out over a period of time of one cycle depending on the frequency. The resultant impedance value calculated for the first measurement electrode is compared against a threshold value to determine whether the electrode is providing as clear a signal as possible for accurate EEG or other physiological signal display. This threshold value is determined by the application as to the sensitivity necessary to provide a good physiological signal. If the electrical impedance calculated in the first measurement electrode is too high, then a technician or operator is notified and he or she decides what type of action is required to renew the quality of the signal. This process is described in greater detail in U.S. Patent Application Publication No. 2011/0295096 A1, which is incorporated by reference.

Additionally, in many embodiments, the physiological signal monitor should have an artifact detection and/or removal system which differentiates between a normal (or abnormal) physiological brain activity and artifacts or noise caused by various sources of interference. The process of artifact detection is described in greater detail in U.S. Patent Publication No. 2011/0295142 A1, which is incorporated by reference.

Further, many embodiments of the present invention provide a cortical suppression detection function to monitor and notify the user when a subject's brain function is suppressed below a threshold level, or when the EEG signal amplitude drops below a certain level. Suppression may be indicative of severe brain trauma such as traumatic brain injury (TBI), over-sedation or anesthesia over-dosing, or the like. In order to provide the suppression detection function, such embodiments may involve computing the first derivative of the physiological or sensor signal. Most embodiments utilize the first derivative, though some embodiments may use a higher derivative. Utilizing the first derivative rather than the raw (or filtered) EEG signals has been shown to remove baseline wandering and thus renders the analysis more accurate and reliable. The step of computing the first or higher derivative of the signal is performed on a processor, in real time, and substantially at the same time as the signal is being acquired. Substantially at the same time means that immediately as the signal is acquired by the circuitry and apparatus described above, the processor computes the appropriate derivative of that signal. Once the desired level of derivative has been computed, an epoch of predetermined size of the derivative of the EEG signal is analyzed using at least one suppression detection parameter, the at least one suppression detection parameter being used to detect suppression in the EEG signal. The suppression detection measure can be virtually any type of operator or algorithm which is capable of detecting the drastic changes in the EEG signal which may be representative of burst and/or suppression periods. Such suppression detection measures may include, but are not limited to the median absolute value, the peak-to-peak time measurement, root mean square (RMS), spectral measures, entropy measures, energy operators, and the like. Preferably, at least one suppression detection measure used is the median absolute value of the first derivative of the EEG signal. The median absolute value is a robust measure of the rate of change of EEG, is less sensitive to outliers, and corresponds with the visual recognition rules of suppression detection. Thus, as the EEG, or other physiological signal, is acquired, the processor first calculates the desired derivative of that signal, and essentially simultaneously computes at least the median absolute value of that first derivative signal. Next, such embodiments utilize the above calculated suppression detection measure(s) (e.g., median absolute value) for the detection of suppression periods in the EEG signal. If the above calculated suppression detection measure is below a predetermined threshold for a predetermined amount of time, then that particular epoch is determined to be suppression. Some embodiments include a step in which artifacts are detected and identified, and are not counted as periods of burst activity. These artifacts may be those that were not detected by the front-end filtering, or new additional artifacts that corrupt the signal after initial filtering. In this optional step, the present invention differentiates between such artifacts and burst activity. This means that the system does not count an aberrant artifact as burst activity and thus effect the detection of burst and suppression periods and their durations. This is another step to increase the accuracy of the invention in environments that create artifacts in the EEG signal. Some embodiments of the present invention further include a step by which the thresholds used for detecting a burst or suppression period are automatically relaxed or tightened based on environmental factors. For example, if the signal contains a particularly strong or high amplitude period of burst activity, the threshold may be relaxed so the results of the detection methods are not artificially skewed or misidentified. This process is described in greater detail in U.S. patent application Ser. No. 13/216,755, which is incorporated by reference.

Various embodiments of the present invention specifically rely on detection of suppression of the physiological signal. Burst suppression detection is generally based on detection of periods of high activity alternating with periods of no activity of a physiological signal. Burst suppression is most typically discussed in regards to EEG signals, though other physiological signals exhibit the same or similar characteristics under certain conditions as well. Therefore, burst suppression is most notably useful in EEG analysis, but the same principles can be applied to most physiological signals, such as EKG, EMG, EOG, and the like. One step in suppression detection involves computing with a processor, substantially at the same time as the signal is acquired, the first derivative of the physiological or sensor signal. Most embodiments utilize the first derivative, though some embodiments may use a higher derivative. Utilizing the first derivative rather than the raw (or filtered) EEG signals has been shown to remove baseline wandering and thus renders the analysis more accurate and reliable. In addition, the surface EEG signals are the time-varying signals that reflect the fluctuations in the number of activated neurons or the alternating component of the mean soma potential over time. The first derivative of EEG signal has been shown to be strongly linked to the mean soma potential based on Cellular Automaton (CA) simulations of cortical function. The step of computing the first or second derivative of the signal is performed on a processor, in real time, and substantially at the same time as the signal is being acquired. Substantially at the same time means that immediately as the signal is acquired by the circuitry and apparatus described above, the processor computes the appropriate derivative of that signal.

In various embodiments of the present invention, the acquired EEG signal may or may not be filtered prior to computing the first (or higher) derivative and analyzing the signal. In those embodiments which require signal filtering, such filtering is performed by means of a low-pass filter used to remove high frequency (HF) interference from the EEG signal. Examples of HF interference that may need to be filtered out of the EEG signal include other physiological signals such as electromyographic (EMG) signals, as well as outside HF interference such as background electrical noise and noise from electro-surgical units (ESUs). Preferably, when filtering is performed, the low-pass filter is set to allow EEG signals with a frequency of 32 Hz and less to pass. More preferably, the filter allows EEG signals with a frequency of 30 Hz and less to pass. More preferably still, the low-pass filter allows EEG signals with a frequency of 24 Hz and less to pass. Even more preferably, the low-pass filter allows EEG signals with a frequency of 16 Hz and less to pass.

Another step in various embodiments involves analyzing an epoch of predetermined size of the first derivative of the EEG signal using at least one suppression detection parameter, the at least one suppression detection parameter being used to detect suppression in the EEG signal. The suppression detection measure can be virtually any type of operator or algorithm which is capable of detecting the drastic changes in the EEG signal which may be representative of burst and suppression periods. Such suppression detection measures may include, but are not limited to the median absolute value, the peak-to-peak time measurement, root mean square (RMS), spectral measures, entropy measures, energy operators, and the like. Preferably, at least one suppression detection measure used is the median absolute value of the first derivative of the EEG signal. The median absolute value is a robust measure of the rate of change of EEG, is less sensitive to outliers, and corresponds with the visual recognition rules of suppression detection. Thus, as the EEG, or other physiological signal, is acquired, the processor first calculates the first derivative of that signal, and essentially simultaneously computes at least the median absolute value of that first derivative signal.

Still another step in various embodiments of the present invention involves utilizing the above calculated suppression detection measure (i.e., median absolute value) for the detection of suppression periods in the EEG signal. If the above calculated suppression detection measure (i.e., median absolute value) is below a predetermined threshold for a predetermined amount of time, then that particular epoch is determined to be suppression.

Some embodiments include a step in which the suppression periods are confirmed by the existence of burst periods in the last minute to ensure that low-amplitude EEG activity is not detected as suppression, while still making sure that slight EEG activity during suppression periods between the bursts doesn't preclude the detection of suppression. If the above calculated suppression detection measure (i.e., median absolute value) is above another predetermined threshold for a predetermined amount of time, then that particular epoch is determined to be burst. Preferably, the suppression periods are confirmed based on at least 10 seconds of burst in the last minute. More preferably, the suppression periods are confirmed based on at least 5 seconds of burst in the last minute. More preferably still, the suppression periods are confirmed based on at least 3 seconds of burst in the last minute. Even more preferably, the suppression periods are confirmed based on at least 1 second of burst in the last minute. More preferably yet, the suppression periods are confirmed based on at least 0.5 seconds of burst in the last minute. Even more preferably still, the suppression periods are confirmed based on at least 0.25 seconds of burst in the last minute.

Some embodiments include a step in which artifacts are detected and identified, and are not counted as periods of burst activity. These artifacts may be those that were not detected by the front-end filtering, or new additional artifacts that corrupt the signal after initial filtering. In this optional step, the present invention differentiates between such artifacts and burst activity. This means that the system does not count an aberrant artifact as burst activity and thus effect the detection of burst and suppression periods and their durations. This is another step to increase the accuracy of the invention in environments that create artifacts in the EEG signal.

Some embodiments of the present invention further include a step by which the thresholds used for detecting a burst or suppression period are automatically relaxed or tightened based on environmental factors. For example, if the signal contains a particularly strong or high amplitude period of burst activity, the threshold may be relaxed so the results of the detection methods are not artificially skewed or misidentified.

Still further embodiments of the present invention may involve using the second-derivative of the EEG signal to perform the suppression detection methods. In such embodiments, similar methods may applied wherein suppression detection measures such as the median absolute value, mean, median, RMS, peak to peak, spectral measures, entropy measures, energy operators, or the like are used to calculate their respective values, and those values compared against appropriate thresholds to determine whether suppression or detection is occurring.

Still another step in various embodiments of the present invention involves outputting a signal, preferably through some variety of output devices or combination of devices capable of providing an alarm or signal, where the signal is based at least in part on the occurrence of suppression in the EEG signal to a device for communicating the outputted signal to a clinician monitoring the patient. The output device may be a visual alarm or signal display such as a monitor or lights, an audio device such as a speaker or audio message, a tactile output device such as a vibrational motor (similar to a cellular phone vibration ring notification), or a combination thereof. This output signal may be any form of signal designed to get the clinician's attention and alert her to the fact that suppression has recently or is presently occurred. Preferably, the output signal is the percentage of suppression detected in the EEG signal during the last minute, known as suppression ratio (SR). It may also include audio warnings or alarms, or visual indicators on a monitor such as a text warning, flashing windows, colors, and the like, or any combination thereof.

Other embodiments may include the step of outputting a signal based at least in part on the occurrence of suppression in the EEG signal to a device for controlling the patient's level of anesthesia and amount of suppression. In this step, rather than, or more preferably in addition to alerting a clinician to the occurrence of suppression in a subject under anesthesia, the subject is instead attached to a closed-loop, or semi-closed-loop drug delivery device which automatically controls the amount of sedative or anesthetic being administered to the subject.

Some embodiments may utilize a bilateral monitoring method to measure EEG signals from the two hemispheres (left and right) of a subject's brain independently and simultaneously. In such embodiments, at least three electrodes (or sensors) are utilized, one measurement EEG electrode to measure EEG signals of the left hemisphere, one measurement EEG electrode to measure the EEG signals of the right hemisphere, and one reference electrode. Such embodiments, preferably, the physiological electrodes or other sensors are placed on the subject's head with at least one measurement electrode on each side of the subject's head (i.e. left and right sides as divided by the sagittal physiological plane). Also preferably, at least one reference electrode needs to be placed in order to obtain and measure the differential EEG signals from each of the measurement electrodes. In order to be able to compare the signals from the left and right hemispheres of the subject's brain, the reference electrode is preferably placed as close as possible to the center of the subject's head. This placement should coincide with the location of the longitudinal fissure. When placed as close to the longitudinal fissure as possible, the reference electrode will receive EEG signals from both hemispheres of the subject's brain, and therefore produces a common signal that can be used to create accurate and comparable differential calculations between the EEG signals measured from each individual brain hemisphere. This process is described in greater detail in U.S. Patent Application Publication No. 2011/0130675 A1, which is incorporated by reference.

Many embodiments of the present invention include brain function monitoring algorithms. The brain function monitoring algorithms use the acquired EEG signals, and process them specifically to determine the subject's brain state, presence and/or level of injury (e.g., TBI) or other abnormal function (e.g., seizure). Examples of some algorithms that may be utilized for brain dysfunction detection are included in U.S. patent application Ser. No. 12/259,652, and U.S. patent application Ser. No. 13/731,315, which are herein incorporated by reference, though other similar algorithms known to those skilled in the art may be used as well. In many embodiments, the same or other algorithms may include the means to determine the level of cortical activity of the subject in order to automatically adjust and control the delivery of drugs to maintain a desired or predetermined level of sedation, or a desired or predetermined depth of anesthesia.

In many embodiments of the present invention, the display device may be substituted for an Integrated Monitoring and Infusion System (IMIS). The IMIS comprises many of the above components in order to perform signal acquisition, pre-processing, analysis, make status determinations, monitor a subject's brain function, and to display various signals and/or indicators. In other words, the IMIS essentially comprises all of the display device functions and features, but also incorporates several additional components, features, and capabilities to perform additional functions of determining a desired or predetermined level of cortical activity, monitoring the subject's cortical activity level, and automatically adjusting the delivery of sedative, anesthetic, and/or analgesic drugs to maintain that desired or predetermined level of cortical activity. Such system can also be used to drive a patient to a new cortical activity target that is more adequate for the clinical situation.

The IMIS embeds one or more control algorithms into a control module, which allows for closed-loop operation; however, in case of adverse conditions, partial or total system failures, or other system errors, the closed-loop function may be overridden and the system controlled manually by the caregiver. By closed-loop, it is intended that the system operate automatically, continuously, and without human interaction once the system has been applied to a subject and set into motion. The control module is designed to regulate the infusion rates of an intravenous hypnotic (sedation or anesthetic) and optionally also an opioid (analgesic) drug. In a preferred embodiment, both a hypnotic and an analgesic drug are administered by individual infusion pumps (described below). The administration of both drugs is typically required to provide a state of balanced anesthesia to the subject, where the subject neither perceives nor recalls noxious stimulation. A controller is used to govern the administration of the anesthetic or sedative medication(s) or drug(s). The controller uses various forms of inputs, such as programs or commands from a user (e.g., label indications based on drug manufacturer recommendations, patient demographics, and the like) and/or measured values from the system (e.g., EEG, EKG or other signals), and adjusts the administration of the anesthetic or sedative based on those inputs. Basing controller and pump operation on the manufacturer recommendations allows the system to ensure that the particular anesthetic or sedative is used according to properly tested guidelines and that the system cannot exceed the recommended maximum values indicated. The controller uses a measurement of the cortical activity of the subject. This measurement can be based on spectral or bispectral analyses, or preferably using wavelet analysis, or any of the other measurements described above, either individually, or in combinations thereof. Ideally, an index of cortical activity used in a closed-loop application should introduce no delay and be linear and time-invariant (LTI) across its whole operating range.

One such EEG index that complies with these requirements is the $WAV_{CNS}$ index, developed by some of the applicants. The $WAV_{CNS}$ index quantifies the effects of anesthesia drugs on the brain using wavelet analysis of frontal EEG signals. It is expressed in a 100-0 scale where "100" represents the awake conscious state and "0" represents the total suppression of cortical activity. A suitable state for performing surgical procedures (i.e., general anesthesia) is between 40 and 60, while a sedated subject is between 60 and 80. A conscious subject produces a value well above 80, while subjects induced into deep coma (e.g., for stroke surgery or refractory seizure control) would have $WAV_{CNS}$ values below 10. Wavelet analysis is a powerful signal processing technique particularly well suited for non-stationary EEG signals. The wavelets are able to simultaneously and rapidly characterize changes in both time and frequency, which more traditional spectral analyses are typically unable to track timely. The $WAV_{CNS}$ rapidly captures fast changes in cortical activity. Another particularly important advantage of the $WAV_{CNS}$ quantifier lies in its consistent and well-defined transient behavior during patient state changes. The only dynamic difference between the physiological effect and its quantification through the $WAV_{CNS}$ algorithm is due to the post-analysis trending filter, which is well-defined, linear and time-invariant. Preferably, feedback quantities used for regulation (i.e., in closed-loop systems) should be LTI to ensure that their input-versus-output relationship can be accounted for by the controller, and that they do not add uncertainty. An ideal sensor for control should not introduce non-linearities (especially discontinuities) and should not introduce (unknown and variable) additional delay. From a control perspective, cortical activity sensors that are LTI represent the best-case scenario. Non-LTI sensors, on the other hand, introduce uncertainty in the system, which leads to instability if not properly accounted for, and/or a reduction in the controller performance. A non-LTI brain function monitor used in a closed-loop application could result in an inaccurate and/or delayed EEG interpretation during sudden changes in cortical activity (due to, e.g., a sudden change in drug administration or change in surgical stimulation). Consequently, in embodiments performing automated sedation control, the overall regulation of anesthetic delivery would be more prone to instability and therefore less safe. The existence of a reliable mathematical function relating a physiological change in drug effect and its corresponding quantification by the $WAV_{CNS}$ means that the effect of the monitoring technology can be fully accounted for in the controller. In addition, it is important that the cortical activity sensing technology does not introduce additional uncertainty in the system, which will ultimately provide better closed-loop performances. Though the $WAV_{CNS}$ index is preferred, other indexes or indices describing a subject's brain or cortical activity can be envisioned and used in conjunction with the present invention, for example the BIS index.

While a single measure can be used, it may be preferable to use a bilateral measure of the cortical activity in order to provide redundancy in the system. In healthy individuals, the left and right hemisphere measures should be equivalent, e.g., in terms of $WAV_{CNS}$, to within a defined degree or threshold. The caregiver could then set the system to operate based on the right hemisphere measure, or the left hemisphere measure, individually. Preferably, the system uses both measures, and outputs a warning to the caregiver and/or automatically adjusts the infusion of hypnotic and/or sedation drugs (in some embodiments) when both measures are significantly different. Preferably, such warnings and/or automatic control are triggered when the difference between the left and right hemisphere measures is greater than 5 percent. More preferably, the warning and/or controls are triggered when the difference is greater than 10 percent. Still more preferably, the warning and/or controls are triggered when the difference is greater than 12 percent. Even more preferably, the warning and/or controls are triggered when the difference is greater than 15 percent. Even still more preferably, the warning and/or controls are triggered when the difference is greater than 20 percent. Such significant difference could be the result of heavy artifact activity in one channel, or an existing or developing neuro-pathology. Alternatively, the control module may continuously assess the quality of the EEG signals from both channels, and automatically use the best channel for its feedback measure. Alternatively, in other embodiments, the system may average both measures in order to further limit the measurement noise.

The control module then calculates the difference between a predetermined set point defined by the caregiver or pre-programmed into the system, and the feedback measure. A control algorithm will then calculate an adequate modification of the infusion rates of either one or both drugs, either using a standard proportional-integrative-derivative (PID) control structure, or a more complex control structure based on robust control methods to guarantee stability in view of subject variability. A standard PID is a control loop feedback system that calculates an "error" value as the difference between a measured variable and a desired or predetermined set point using at least three constant parameters: proportional error value, integral error value, and derivative error value. These three parameters are then weighted and summed and that sum is used to automatically adjust the infusion rates to minimize the error value.

In a preferred embodiment, a robust controller is specifically tuned to remain stable in view of a certain degree of variability. In some instances, the expected amount of subject variability for which the controller needs to account can be reduced by providing or inputting some subject-specific information to the system, such as the subject's age, weight, height, gender, ethnicity, etc. via an input or interface device or component. Based on this information, the robust controller can be more aggressive.

In some instance, a robust PID controller can be designed to effectively account for patient variability in such a way that a unique controller can be used for a wide population of patients. Patient variability is probably the most challenging aspect in "closing the loop." Quantifying this variability and expressing it as a system uncertainty is a first step in order to prove the stability of the controller when closing the loop. Once a robust design is achieved, performance can be assessed to verify that it meets clinical expectations. Methods and systems for quantifying patient variability are taught in U.S. patent application Ser. No. 13/962,565, to which the present application claims priority as a continuation-in-part, and which is incorporated herein by reference in its entirety.

An important safety aspect is also to limit the control action of the controller. For instance, the caregiver can define upper and lower infusion rates that the controller cannot exceed without the caregiver's acknowledgement. Preferably, the caregiver could define upper and lower effect-site or plasma concentrations beyond which the controller should not operate. In this case, the controller would not be able to derive an infusion profile which would lead to a violation of these upper and lower concentration bounds. The effect-site or plasma concentration may be either estimated using pharmacokinetic and/or pharmacodynamic models, or directly measured through blood analysis or other biomarkers. Alternatively, these limits may be predetermined and preprogrammed into the system.

In a preferred embodiment, the safety limits are directly calculated based on the drug manufacturer's recommendation, or label indications as provided with the medication. These recommendations are typically based on the patient's weight, age, height, gender and overall health status. By entering this information in the system, the user will be proposed a de facto minimum and/or maximum infusion rate, or drug dosage that the system will not exceed. These pre-calculated safety limits may be overridden by the user at any time.

The control module should preferably take as input the effective infusion rate delivered by the infusion pump(s), and not the rate determined by the controller. The effective rate is either measured by the pump, using appropriate sensors, or is simply the rate at which the pump currently operates. The effective rate may be different than the rate the controller outputs. Preferably, the closed-loop system should not assume the rate it has sent the infusion pump is equal to the effective rate. In case a syringe is empty, or if the caregiver may stop the pump manually, the controller may compensate for the lack of drug injected to the subject by catching up once the pump is operational again. This is typically done through the predictive part of the control algorithm. For safety reasons, any issue with the infusion pump(s), such as an empty syringe, a line occlusion, loss of communication/power, etc., should be systematically delivered to the caregiver. Such delivery can take place via audio signal, visual signal on the display, wireless communication, or the like. Another safety issue is to validate that each pump is delivering the right drug. This can be done by prompting the caregiver to validate the drug and drug concentration prior to starting the case.

Another useful feature of the control module is its ability to detect out-of-the-ordinary subjects, e.g., subjects which may require much higher or much lower drug administration. Such subjects may be suffering from an underlying pathology, for example. The control module could automatically and continuously measure the difference between the amount of drug effectively administered, and the amount of drug that would have been administered in open-loop, i.e., based on a pharmacokinetic and pharmacodynamic model of the subject. If there is a large difference between the two, the subject differs significantly from the norm. This information may be useful to the caregiver, as it may denote an abnormal volemia, or metabolism.

As noted above, many embodiments of the present invention further comprise at least one drug infusion device. The drug infusion devices envisioned for use with these embodiments may be of a typical syringe infusion pump presently known to those of skill in the art. Such infusion pumps will be particularly suited for embodiments wherein the IMIS is integrated into a medical transport or evacuation vehicle, and thus wherein the IMIS may be a larger system that is mounted in a stationary manner within said vehicle. However, many other embodiments will utilize a miniaturized, portable infusion pump(s) in order to provide sedation control and/or pain control in the field until such medical transport can arrive, or the subject can be delivered to a higher echelon of medical care.

In the envisioned syringe infusion pumps, a piston applies pressure on a disposable syringe filled with the drug to be delivered, either a hypnotic (sedative or anesthetic), or analgesic drug. Infusion pumps can allow for very small rates of delivery (i.e., less than 0.1 milliliters per hour) or larger rates of delivery (i.e., more than 1,000 milliliters per hour), which makes them ideal for delivering either rapid boluses or much slower and longer infusions. The infusion pump mechanism itself is preferably very simple and is constructed of a light frame of metal (e.g., aluminum) or plastic, where a cursor moves up and down along a screw whose angular position and rotational speed is controlled through a gear connected to a brushless stepper motor. The cursor is attached to the syringe plunger such that pressure on the plunger can be exerted when the stepper motor rotates. When such pressure is placed on the syringe plunger, it slowly forces the plunger through the syringe, thus dispensing the particular drug out of the needle end of the syringe.

Although syringe pumps are envisioned for most embodiments, in some embodiments other types of pumps may be used. Peristaltic pumps provide the advantage of permitting a very large reservoir, and may be used when it is anticipated that a large quantity of drug may need to be delivered over an extended period of time. Other embodiments may utilize a reservoir with a specific, pre-determined volume of drug or medication to be delivered to a subject. For example, a small reservoir containing several doses, enough for medical transportation to a stationary care environment, may be used in certain embodiments rather than a large-volume reservoir for continued use over a period of time. Volumetric pumps, gravity-based pumps, or any other type of pump known to those skilled in the art might also be used. Drug delivery may also be performed by providing a vaporized, atomized or gaseous drug which is inhaled by the patient or subject to induce anesthesia or sedation. In such case, the delivery of the drug may be made by means of an oral or oral-nasal mask, a nasal cannula, or other suitable means, and the IMIS would include, as appropriate, a pressurized canister for the gaseous drug, or a vaporizer or atomizer. The closed-loop delivery system would then control a pressure valve or other flow control apparatus, instead of (or in addition to) a syringe pump or similar pump, in order to regulate the delivery of the drug to the patient or subject. In such oral or oral-nasal delivery embodiments, the entire system may be integrated as a face mask that secures to the head with an elastic band or strap, or other suitable attachment methodology or apparatus that simultaneously ensures the appropriate EEG sensor connections on the forehead and/or temples and securely seals the delivery system around the airway entrance(s). Preferably, in such embodiments, the entire system is integrated into the face mask, providing for ease of application and use in a battlefield or other emergency scenario to provide fast and easy administration of closed-loop sedation or anesthesia.

In many embodiments, the particular type or variety of drug delivery pump(s) chosen may be directly influenced by the type of drug being administered. Thus, it may be preferable for the system to be modular in nature such that several types of drug infusion pumps may be used simply by attaching the different pump to a base unit. Also preferably, the system is designed to work with and administer a large variety of types of drugs to a subject. One particular class of drugs the systems, devices and methods of the present invention are designed to administer includes vapor or inhaled sedatives and anesthetics, which includes drugs such as, for example, sevoflurane, isoflurene, desflurane, and other like drugs. Another class of drugs the systems, devices and methods of the present invention are designed to administer includes intravenous sedatives and anesthetics, which includes drugs such as, for example, barbiturates, benzodiazepines, phencyclidine, carboxylated imidazole, isopropylphenol, dexmedetomidine, and other like drugs. Still another class of drugs the systems, devices and methods of the present invention are designed to administer includes opioids, which includes drugs such as, for example, morphine, fentanyl, alfentanil, sufentanil, remifentanil, and other like drugs.

In practice, infusion pumps for human use must be certified to have no single point of failure. That is, no single cause of failure should cause the pump to silently fail to operate correctly. The infusion pump should at least stop pumping and make at least an audible error indication. This is a minimum requirement on all human-rated infusion pumps. At a minimum, the angular velocity of the motor drive and the cursor position must be measured in real-time to verify that they both correspond to the expected infusion rate set by the IMIS. Any difference between the two measures automatically shuts down the power to the drive and outputs a visual and/or audible alarm.

The infusion pump(s) of the present invention further comprise additional sensors and features that are required for use of such infusion pumps on humans: (1) an anti-free-flow device to prevent blood from draining from the human subject, or prevent the drug from freely entering the human subject, when the infusion pump is being set up; (2) a pressure sensor to detect occlusion (e.g., vein blockage, or kink in the line); and (3) a syringe lock mechanism to verify that the syringe is properly placed and to check its outer diameter. In addition, the IMIS system may also be capable of battery operation so that drugs can be infused to patients during power failure. The IMIS will also keep a detailed log of the pump operation, including start and end time of infusion, infusion rates, total volume administered, etc. This detailed log will be stored along with other data, as described above, on the internal removable or non-removable memory. Alternatively, or in conjunction with the internal memory of the system, the IMIS will be capable of maintaining a very large database using a large capacity solid-state drive.

It should be noted that, while the IMIS depicted in FIGS. 6A-6J integrates the infusion mechanism for ease-of-use and limit size and weight, other embodiments exist where the IMIS controls external infusion systems via, for example, a parallel or serial bus interface (e.g., USB, RS232, or the like), a network interface (TCP/IP protocol), or via a wireless interface (e.g., Wi-Fi, Bluetooth, or the like).

In most embodiments, the IMIS embeds a graphical user interface (GUI), such as the one depicted in FIG. 8. The user interface, at a minimum, displays one or more EEG signals that are used to make the cortical activity level determination. The interface also displays the real-time cortical activity level and its time course over time. A panel gives the user the ability of turning on or off the closed-loop feature, or to manually change the infusion rate. An emergency stop button allows the user to stop the infusion. Conversely, a bolus button allows the user to deliver a large amount of drugs in a short amount of time, e.g., to induce a patient into an anesthetic depth. An indicator on the cortical activity level time course shows the range of cortical activity level targeted by the system. Optionally, other graphs showing the estimated plasma and effect-site concentrations can be displayed to aid in the manual operation of the system. Also optionally, a future predicted time course of the plasma and effect-site concentrations, and/or effect can be displayed based on pre-programmed models. The future predicted time course can be useful to determine, for example, how long it will take to bring a patient into a lighter or deeper cortical activity level range, or to determine how long the closed-loop controller will take to bring the patient into the targeted zone. Another useful feature of the GUI is the creation of a data log. With each case, a data archive should be created containing at the very least the time course of the feedback variable (e.g., the $WAV_{CNS}$ index) as well as the controller outputs and the infusion pump rates. In some embodiments, the data log should also contain the user actions on the system, as well as a list of all the alarms and warnings during the case. The data log can be used for data audit purposes, or to serve as basis in future improvement of the system.

In a preferred embodiment, the GUI should be developed in such a way to minimize user confusion and user error while ensuring that the user verifies all the proper settings on the pump(s) and of the closed-loop system. A confirmation based GUI can be envisioned, where the user is asked to confirm his/her choices before being allowed to move to the next stage. Once all the confirmations have been obtained, the system allows the user to "close the loop."

The closed-loop feature of the IMIS is particularly useful in patients for whom the administration of total intravenous anesthesia (TIVA) is difficult or complicated by existing co-morbidities, in particular, for patients suffering from hepatic/renal failure, hemodynamic instability, or hypovolemia.

Although the illustrations show a GUI integrated into the IMIS, the IMIS in some embodiments may be controlled by a separate display/interface device, such as a smartphone, tablet computer, portable computer, medical grade computer monitor, or other similar device, which is connected to the IMIS by wired or wireless connection.

Preferably, the IMIS calculates the drugs minimum and maximum dosage as recommended by the drug manufacturer, based on the weight of the patient or subject, and/or other parameters as discussed herein or as would be known to a person skilled in the art. These one or more parameters may be entered by the user or responder prior to the administration of drug to the patient or subject through the GUI. The GUI preferably asks the user or responder to confirm entered parameters prior to administration of drug to the patient or subject, and provides for sensible error-checking to prevent entry of unlikely parameter values or combinations of parameter values. For example, an entry of 2,000 pounds for human subject weight is likely to be the result of a miss-entry, such as one too many zeroes input for the weight value. The user of the system may override the minimum and maximum dosages at any time. Preferably, the device is configured so as to make it impossible to administer the drug outside of either the drug manufacturer recommended dosages or outside the dosing limits specified by the user. As such, the IMIS provides for safety and risk mitigation.

Given that the system is designed to keep the subject in a preferred range of anesthetic or sedative depth, it is important to consider what occurs when the subject goes too deep into anesthesia or sedation. Such occurrence is referred to as suppression, or burst suppression. Suppression, particularly of EEG activity, is indicative of anesthesia or sedation that is so deep as to effectively stop brain function. Such condition might be desirable, for example where the subject is placed into a medically induced coma. However, for patients where such a level of anesthesia or sedation is not desired or predetermined, suppression can lead to injury and long-lasting harmful effects to the patient. Thus, many embodiments of the present invention further include the ability for the system to detect burst suppression, to automatically cease or reduce operation of the infusion pumps to stop administration of additional anesthetic or sedative medication or drug, and to alert or otherwise signal a clinician to notify that suppression has been detected in order for the clinician to tend to the patient and mitigate any harmful effects of the suppression. Effectively, the physiological signal monitor acquires the physiological signal and the processor analyzes the signal, preferably in real-time, at least partially attempting to detect burst suppression. When burst-suppression is detected, the processor sends a signal to the controller instructing the controller to cease or reduce administration of the anesthetic or sedative by stopping or ceasing operation of the infusion pump. In some embodiments, the system may also cease or reduce operation of the infusion pump when one of the programmed label indications for the particular drug or medication is reached. For example, if the system detects that the maximum recommended dose volume has been reached, then the pump would be stopped and no additional drug or medication will be administered until an appropriate amount of time has passed so as to allow for another dose, or if a clinician overrides or changes the settings of the system. Additionally, in many embodiments, the system further provides an alarm or some other signal to a clinician indicating that suppression has been detected and that the subject needs immediate attention to mitigate the suppression of the physiological signal.

For these embodiments where the system is designed to cease or reduce administration of the drug(s) or medication (s) in response to detection of some adverse condition, such as burst suppression, the process for resuming normal function of the system to provide further anesthesia or sedation may vary based on whether the system is fully closed-loop or semi-closed or open-loop, or based on whether the embodiment calls for multiple layers of safety before resuming function. One method of resuming operation of the system is to require the clinician to manually reset or instruct the system to be able to increase or resume administration of the anesthetic or sedative. This method is likely necessary for semi-closed and open-loop systems, but may be optional for a normally fully closed-loop system. Once the system detects an adverse condition, such as burst suppression, and ceases or reduces administration of the drug(s), the alarm notifies the clinician of the condition, and the clinician must respond to halt the alarm or signal and tend to the subject. Once the subject has been checked as in safe condition, the clinician must then manually instruct the system to increase or resume administration of the drug. Without direct instruction from the clinician, the system will remain in an off or standby mode and not administer any further drug or medication. This ensures that only when the clinician specifically verifies that the subject is stable and not in further danger of harm or injury that the system can resume providing anesthesia or sedation to the subject. The manner in which the clinician interacts with the system to instruct it to resume depends on the specific embodiment, and may be done locally by direct interaction the interface or controls of the system, or may be done remotely by way of remote communication with the system from a separate console or device. Fully open-loop systems, in some circumstances, may require clinician instruction to resume or restart, such as if the adverse condition (i.e., burst suppression) is prolonged for a given period of time, if the alarm or signal goes unanswered for too long, or if the adverse condition is detected to be particularly severe, or the like. Such circumstances would dictate, even to a fully closed-loop system that the subject's condition is so dangerous that clinician involvement is necessary to prevent severe harm to the subject. This may effectively render such a system a semi-closed loop system in such instance, but generally the system may operate in a fully closed-loop mode unless extenuating circumstances arise. In normal full closed-loop operation, the system may automatically increase or resume administration of drug(s) or medication(s) after detection of an adverse condition and ceasing of operation. Generally, such embodiments would allow the system to automatically restart if the adverse condition is no longer detected, is particularly mild or non-severe, and/or if other conditions are met that dictate that direct clinician interaction is not entirely or immediately required. The physiological signal monitor and processor would determine that the adverse condition no longer exists, and the processor would then send a signal to the controller to resume function of the infusion pump to continue administering the drug or medication to the subject.

Now referring to the Figures, FIG. 1 depicts one optional design for a non-concentric pumping mechanism to progressively decrease occlusion of the tubing at the exit point in order to reduce or eliminate flow pulsation anomalies in operation of a rotary peristaltic pump for delivering fluids or medication to a subject. This figure presents an eccentric gear mechanism. The depicted gear mechanism comprises a sun gear 105, three planet gears 110, and an annular gear 115. Although three planet gears 110 are depicted, as few as two may be used. The sun gear 105 connects to the drive shaft and/or driver (not shown) of the driver motor (drive shown) and is caused to rotate. The sun gear 105 in turn causes the planet gears 110 to rotate and travel around the interior of the pumping chamber 100. The planet gears are disposed between the sun gear 105 and the annular gear 115 and each gear interlocks via teeth or grooves. As the sun gear 105 rotates, the motion of the teeth or grooves of the sun gear pushes the teeth or grooves of each planet gear 110 and causes them to rotate and move. The annular gear 115 helps provide stability to the entire gear mechanism by preventing the planet gears 110 from shifting, and thus maintains consistent and stead rotation of the gears, and thus movement of the planet gears 110 around the pumping chamber 100. Attached to or integrated into each planet gear 110 is a roller or roller element 120. The roller or roller element 120 is disposed to apply pressure against the tubing (not shown) that is within a tubing groove (not shown) of the pumping chamber 100. The rollers or roller elements 120 apply pressure to the tubing and cause occlusion of the tubing. As the planet gears 110 travel around the pumping chamber 100, the rollers or roller elements 120 travel with the planet gears 110 providing pressure and occlusion to the tubing at their point of contact along the distance traveled. This movement and traveling of the applied pressure points causes the fluids or medication (not shown) to be drawn into the tubing and move through the tubing to be delivered to a subject. The eccentric design depicted is defined as such as a result of the center of rotation of the gear system 140 being offset from the center of the pump mechanism casing (not shown). This offset design causes the gear system to provide varying levels of occlusion of the tubing throughout the travel of the rollers or roller elements 120 around the interior of the pumping chamber 100. Using the eccentric pumping mechanism, the system can be tailored to provide varying levels of occlusion at various points along the tubing in the tubing groove (not shown).

Various points of the pumping chamber 100 can be defined in reference to the tubing and fluids that help describe the operation of this eccentric pumping mechanism. A tubing entry point 125 is the point where the tubing enters the pumping chamber 100 and the tubing groove (not shown) thereof. The rollers or roller elements 120 first contact the tubing at the entry point 125 and cause occlusion of the tubing. As the rollers or roller elements 120 travel around the interior of the pumping chamber 100, the roller or roller element 120 that most recently passed the entry point 125 becomes a "pulling roller" that operates to pull fluids or medication through the tubing into the pumping chamber. A pulling roller remains so until at least the point where it reaches the point of maximum occlusion 135. After a roller or roller element 120 passes the point of maximum occlusion 135, it becomes a "pushing roller" in that it shifts to effectively push the fluid or medication in front of it out of the pumping chamber while a subsequent roller or roller element enters the pumping chamber at the entry point 125 and becomes the pulling roller. The point of maximum occlusion 135 may be a single point or may be a length of the interior of the pumping chamber 100, depending on the embodiment. Some embodiments maintain a steady level of occlusion, which is the maximum occlusion percentage, until some point at which occlusion is decreased, and thus occlusion is at its maximum level from the entry point 125 where the roller or roller element first contacts the tubing until some point where occlusion is begun to be decreased. Other embodiments allow for progressive occlusion increase such that the roller or roller element first contacts the tubing at the entry point 125 and then progressively and preferably continuously increases occlusion of the tubing until the point of maximum occlusion 135. In either such embodiment, occlusion may progressively and preferably continuously be decreased from the point of maximum occlusion 135 to the exit point 130 where the tubing exits the pumping chamber 100. Preferably, occlusion at the exit point 130, or exit occlusion 145, is at most 0%, which corresponds to the tubing being completely open to its original round shape. More preferably, exit occlusion 145 is negative meaning that the roller or roller element 120 is not in contact with the tubing at all, thereby ensuring that the roller or roller element 120 is not causing any occlusion at all. This eccentric design allows for the pumping system to progressively and preferably continuously (e.g., in a linear fashion characterized by a steady rate of decrease of occlusion) decrease the occlusion of the tubing from the point (or distance) of maximum occlusion 135 to the exit point 130 which prevents the occurrence of flow pulsation anomalies caused by a sudden or too rapid decrease in occlusion.

Figure 2:
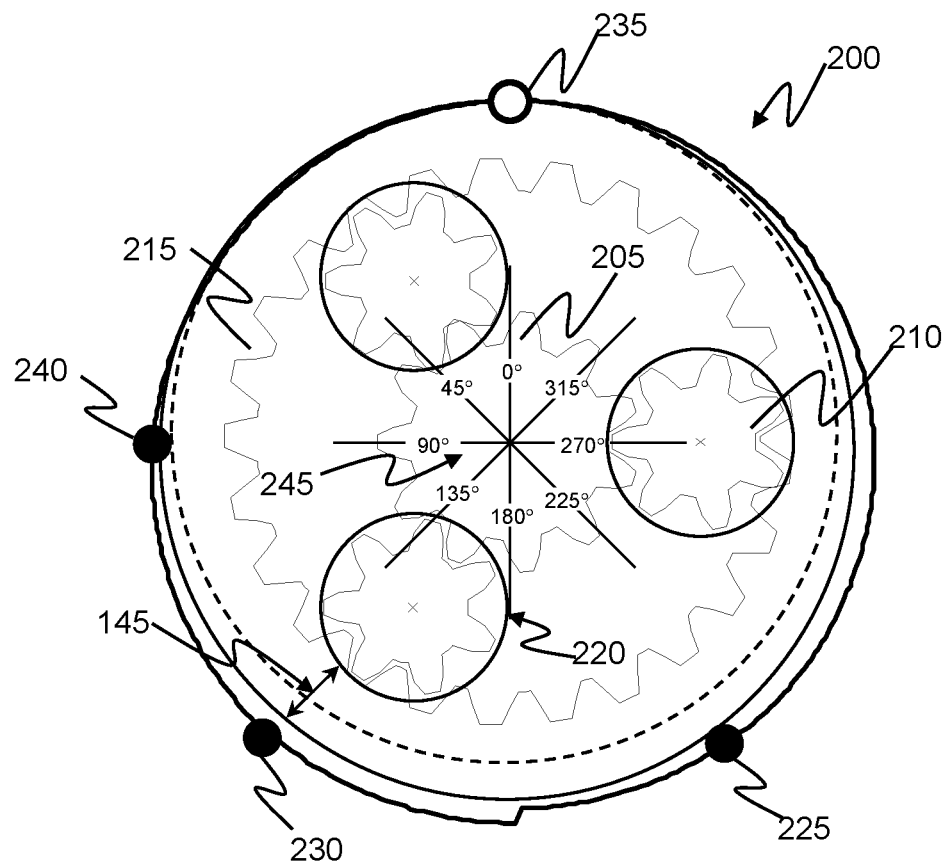
FIG. 2. Diagram depicting a geometric peristaltic pump gear mechanism.

FIG. 2 depicts another optional design for pumping mechanism to progressively decrease occlusion of the tubing at the exit point in order to reduce or eliminate flow pulsation anomalies in operation of a rotary peristaltic pump for delivering fluids or medication to a subject. This figure presents a geometric gear mechanism whereby the pumping chamber 200 is designed to effectively break the chamber 200 geometry into discrete sections, each with a predefined occlusion percentage assigned thereto. Given the circular geometry of the pumping chamber 200, one example of a geometric design would be to break the chamber geometry into 360 segments, and define each with a certain percentage of occlusion to be provided at each section. The gear mechanism then can be designed to provide the desired occlusion percentage at each point along the tubing groove (not shown) of the pumping chamber. The depicted gear mechanism, similar to the eccentric design in FIG. 1, comprises a sun gear 205, three planet gears 210, and an annular gear 215. Although three planet gears 210 are depicted, as few as two may be used. The sun gear 205 connects to the drive shaft and/or driver (FIG. 4, 515) of the driver motor (FIG. 4, 520) and is caused to rotate. The sun gear 205 in turn causes the planet gears 210 to rotate and travel around the interior of the pumping chamber 200. The planet gears are disposed between the sun gear 205 and the annular gear 215 and each gear interlocks via teeth or grooves. As the sun gear 205 rotates, the motion of the teeth or grooves of the sun gear pushes the teeth or grooves of each planet gear 210 and causes them to rotate and move. The annular gear 215 helps provide stability to the entire gear mechanism by preventing the planet gears 210 from shifting, and thus maintains consistent and stead rotation of the gears, and thus movement of the planet gears 210 around the pumping chamber 200. Attached to or integrated into each planet gear 210 is a roller or roller element 220. The roller or roller element 220 is disposed to apply pressure against the tubing (not shown) that is within a tubing groove (not shown) of the pumping chamber 200. The rollers or roller elements 220 apply pressure to the tubing and cause occlusion of the tubing. The roller element 220 further acts as an anti-free-flow device in that it occludes the tubing and prevents backward free-flow of fluids in the tubing. As the planet gears 210 travel around the pumping chamber 200, the rollers or roller elements 220 travel with the planet gears 210 providing pressure and occlusion to the tubing at their point of contact along the distance traveled. This movement and traveling of the applied pressure points causes the fluids or medication (not shown) to be drawn into the tubing and move through the tubing to be delivered to a subject. The geometric design depicted is defined as such as a result of the pumping chamber 200 geometry being broken into discrete segments as described above with the center of the drive shaft or driver (FIG. 4, 515) of the pump as a reference. This design, therefore, can be either concentric, where the epicyclic gear mechanism (comprising the sun 205, planet 210 and annular 215 gears) shares a center of rotation 245 with the casing (not shown) of the administration set or cartridge, or can be eccentric as in the embodiment described in FIG. 1. The geometric design ensures that the system can be tailored to provide varying levels of occlusion at various points along the tubing in the tubing groove (not shown).

Various points of the pumping chamber 200 can be defined in reference to the tubing and fluids that help describe the operation of this eccentric pumping mechanism. A tubing entry point 225 is the point where the tubing enters the pumping chamber 200 and the tubing groove (not shown) thereof. The rollers or roller elements 220 first contact the tubing at the entry point 225 and cause occlusion of the tubing. As the rollers or roller elements 220 travel around the interior of the pumping chamber 200, the roller or roller element 220 that most recently passed the entry point 225 becomes a "pulling roller" that operates to pull fluids or medication through the tubing into the pumping chamber. A pulling roller remains so until at least the point where it reaches the point of maximum occlusion 235. After a roller or roller element 220 passes the point of maximum occlusion 235, it becomes a "pushing roller" in that it shifts to effectively push the fluid or medication in front of it out of the pumping chamber while a subsequent roller or roller element enters the pumping chamber at the entry point 225 and becomes the pulling roller. The point of maximum occlusion 235 may be a single point or may be a length of the interior of the pumping chamber 200, depending on the embodiment. Some embodiments maintain a steady level of occlusion, which is the maximum occlusion percentage, until some point at which occlusion is decreased, and thus occlusion is at its maximum level from the entry point 225 where the roller or roller element first contacts the tubing until some point where occlusion is begun to be decreased. Other embodiments allow for progressive occlusion increase such that the roller or roller element first contacts the tubing at the entry point 225 and then progressively and preferably continuously increases occlusion of the tubing until the point of maximum occlusion 235. In either such embodiment, occlusion may progressively and preferably continuously be decreased from the point of maximum occlusion 235 or from some other predefined point of exit occlusion 240, to the exit point 230 where the tubing exits the pumping chamber 200. The geometric design provides the advantage of allowing the occlusion to be progressively decreased over any preferred length of tubing and to be fully released at any point, even prior to the exit point 230. Preferably, occlusion at the exit point 230, or exit occlusion 250, is at most 0%, which corresponds to the tubing being completely open to its original round shape. More preferably, exit occlusion 250 is negative meaning that the roller or roller element 220 is not in contact with the tubing at all, thereby ensuring that the roller or roller element 220 is not causing any occlusion at all. By reaching an exit occlusion 240 of 0%, or even negative occlusion, prior to the exit point 230, the system can ensure that the roller or roller element exiting the pumping chamber does not cause any flow pulsation anomalies because it is no longer in contact with the tube. This geometric design allows for the pumping system to progressively and preferably continuously (e.g., in a linear fashion characterized by a steady rate of decrease of occlusion) decrease the occlusion of the tubing from the point (or distance) of maximum occlusion 235 to the exit point 230 which prevents the occurrence of flow pulsation anomalies caused by a sudden or too rapid decrease in occlusion.

FIGS. 3A-D present multiple views of the exterior of the administration set/cartridge 500 of the present invention: A) cross-section view from top or front with planet gears; B) bottom or back view; C) perspective view of the pump head module showing the pumping mechanics; and D) cross-section view from bottom or back with rollers. FIG. 3A depicts a cross-section view from the top or front of the administration set or cartridge 500 as it would be viewable when inserted into the pump module (505) and viewed directly from the front by a user. It is presented as a cross-section in order to depict the pumping mechanics inside the pump head module which may or may not be visible depending on the embodiment of the pump head module and whether the outer and/or front casing is transparent, semi-transparent, or solid/opaque. The front cover of the administration set or cartridge 500 preferably comprises a transparent or semi-transparent portion 300 through which the pumping mechanism can be viewed by a user. This provides the benefit of allowing the user to determine rapidly whether the system is operational by viewing movement, or lack thereof, of the pumping mechanism inside the pump head module. Through the transparent or semi-transparent portion 300 the gear mechanism is visible, including the sun gear 305, planet gears 310 and possibly the annular gear 315. The rollers or roller elements (not shown) attached to or integrated onto the planet gears 310, depending on the design, may also be visible, and may block or hide the visibility of the planet gears 310 depending on the configuration. In any embodiment with a transparent or semi-transparent portion 300, some portion of the gear mechanism is visible so as to make visual confirmation of pump operation possible by viewing movement of the gears. When the pump is operating, a user can perform a rapid visual check to ensure the gears are moving in order to verify the pump is operational, and quickly move on to other potential issues when troubleshooting issues with delivery of the fluids or medication. The casing of the administration set or cartridge 500 further comprises an entry port 320 and an exit port 325 that provide ingress and egress of the tubing (not shown) into and out of the administration set or cartridge 500. The tubing enters through the entry port 320, preferably traverses a strain relief section (see FIG. 3D), then enters the pumping chamber (as described above) through the entry point (as described above) traverses around the pumping chamber (as described above) in the tubing groove (as described above), exits the pumping chamber at the exit point (as described above), preferably traverses the same or a different strain relief path (see FIG. 3D), and exits the administration set or cartridge 500 through the exit port 325. Further, the outer casing of the administration set or cartridge 500 preferably includes a series of one or more light pipes or channels 330 disposed around the casing in various positions. These light pipes or channels 330 are grooves, apertures or indentures in the casing that allow light to be transmitted from a light source, preferably an LED, integrated into the administration set or cartridge 500 and to be visible from large viewing angles in relation to the front or top of the administration set or cartridge 500. The light source may be embedded in the base (see FIG. 3B) of the administration set or cartridge 500 and can be used to convey various messages to a user based on the color displayed, pattern or sequence of lights shown, or any other arrangement of light displays. The light pipes or channels 330, combined with a preferably tapered front cover of the administration set or cartridge 500 casing, allow for the light to be transmitted from the light sources and to be visible from preferably 360° horizontally (in relation to the front of the administration set or cartridge 500, and from preferably 180° or more vertically where the casing or the pump module 505 itself likely block vertical visibility. Also visible in the depicted embodiment is a locking tab or protrusion 335 that facilitates the twist-and-lock installment and uninstallation of the administration set or cartridge 500 to and from the pump module 505. When the administration set or cartridge 500 is inserted into the pump module 505, a locator ring (see FIG. 3B) secures the administration set or cartridge 500 in the x- and y-axes, and allows the administration set or cartridge 500 to rotate and lock into place when the locking tab or protrusion 335 enters a groove or cavity in the pump module (505) to lock the administration set or cartridge 500 into place in the z-axis. Preferably at least two locking tabs or protrusions 335 are used, though only one is depicted in the drawing.

FIG. 3B depicts the bottom or back view of the administration set or cartridge 500. The bottom or back casing 340 of the administration set or cartridge 500 comprises a locator ring 345 as described herein. The locator ring 345 is preferably an indent or groove in the base of the bottom or back casing 340 of the administration set or cartridge 500 that corresponds to a raised portion or ridge 510 of the pump module (505), and which fit together. When placed into the pump module 505, the administration set or cartridge 500 is preferably locked into place in the x- and y-axes by the locator ring and corresponding raised portion or ridge 510 of the pump. This prevents movement of the administration set or cartridge 500 in the x- and y-axes. Further, when placed in the pump module 505, the administration set or cartridge 500 comprises a driver portion 350 that fits onto the drive shaft or driver of the pump module 505. The driver portion 350 is then rotated by the driver shaft or driver 515 of the pump module 505 and causes the gears to rotate as described herein. Also depicted are signal light sources 355 which operate to provide visual signals, messages or alarms to a user via the light pipes or channels depicted in FIG. 3A. Alternatively, the light sources may not be embedded in or affixed to the bottom or back casing of the administration set or cartridge 500, but rather may be affixed, embedded or integrated into the pump module 505 itself, in which embodiment the circles depicted in this figure would be light pipes or channels allowing the light from the light sources to be transmitted through the light pipes or channels in the bottom or back casing, through the light pipes or channels in the front or top casing, and to be visible to a user. The present figure also shows a locking tab or protrusion 365 which corresponds to a cavity or groove in the pump module 505 to lock the administration set or cartridge 500 into place in the z-axis when the administration set or cartridge 500 is inserted into the pump module 505 and rotated into the locked position as described herein. The present figure further depicts sensor apertures or ports 360. These sensor ports 360 allow for the insertion of pressure pins (not shown) and sensors (not shown) that can be used to detect and measure pressure of the tubing, as applied by the fluids or medication therein. These sensors ports 360, with attendant sensors and pins, would allow the system to measure the pressure and to determine if there is an issue or problem with the level of pressure, which could in turn be used to generate a signal, warning or message related to the pressure issue, which could be communicated via the light sources and light pipes or channels 355.

FIG. 3C portrays a perspective view of the administration set or cartridge 500, formed by a combination of the front/top casing (a cross-section of which is depicted in FIG. 3A) and the back/bottom casing of FIG. 3B. The transparent or semi-transparent portion 370 of the front/top casing allows for visibility of the gear mechanism comprising the sun gear 375, planet gear(s) 380 and possibly the annular gear 385. The light pipes or channels 395 are disposed around the transparent or semi-transparent portion 370 to transmit light from the light source(s) (not shown) and make the light messages, warnings or signals visible from large viewing angles. The entry port 390 allows for the tubing (not shown) to enter the administration set or cartridge 500 to allow the gear mechanism to provide occlusion and cause flow of the fluids or medication through the tubing. The locking tab or protrusion 397 allows for the administration set or cartridge 500 to be locked into place in the z-axis when the administration set or cartridge 500 is inserted into the pump module (505) and rotated along the locator ring (not shown) such that the locking tab or protrusion 397 enters a corresponding cavity or groove in the pump module 505 and prevents movement of the administration set or cartridge 500 in the z-axis.

FIG. 3D presents a cross-section view of the top or front casing of one embodiment of the administration set or cartridge 500 from the back—as opposed to FIG. 3A which is a cross-section view from the front. The casing 400 comprises the annular gear 405 which interconnects with the planet gears (not shown) attached to the rollers or roller elements 455 of the epicyclic gear system, and a tubing groove 410 which provides a pathway for the tubing through the pumping chamber of the administration set or cartridge 500. Further, the entry point 420 and exit point 425 where the tubing enters and exits the pumping chamber, respectively, are shown. As noted, the entry point 420 is where the tubing enters the pumping chamber and the rollers or roller elements 455 first come in contact with the tubing and causes occlusion of the tubing in order to advance the fluid or medication through the tubing. Also as noted, the exit point 425 is where the tubing exits the pumping chamber, and preferably, in accordance with the objectives of the present invention, the tubing is either 0% occluded or has negative occlusion indicating that the roller or roller element is not in contact with the tubing at all, allowing the tubing to be at its original round shape and to minimize or eliminate flow pulsation anomalies. Additionally, the light pipes or channels 415 can be seen which allow light to be transmitted from light source(s) in the bottom or back casing (not shown) or the pump module (not shown) to deliver messages, warnings, signals or alarms to a user of the system as described herein. The present figure further depicts a strain relief path 430 for the tubing. In some embodiments, two different types of tubing may be used: a softer, flexible tubing within the administration set or cartridge 500 and a harder, kink-resistant tubing extending from the fluid or medication source to the administration set or cartridge 500 as well as away from the administration set or cartridge 500 to the delivery point, such as an intravenous needle or the like. In such embodiments, the two types of tubing would be coupled at or near the entry port 435 and the exit port 440 of the administration set or cartridge 500. Such coupling may encounter the issue of the tubes decoupling when presented with a force, typically on the exterior harder, kink-resistant tubing that might pull the coupled tubes apart. The strain relief path 430 helps prevent such decoupling by providing a longer pathway for the interior tubing to travel and by displacing the effect of any force on the tubing that might cause the two tubes to become decoupled. The tubing enters the administration set or cartridge 500 via the entry port 435 and is disposed along the strain relief path 430 and into the pumping chamber via the entry point 420. The solid directional arrows indicate the incoming pathway of the tubing. Similarly, the interior tubing leaves the pumping chamber via the exit point 425, traverses the strain relief path 430, likely stacked on top of or below the incoming portion of the tubing, and exits the administration set or cartridge 500 via the exit port 440. The dotted directional arrows indicate the outgoing pathway of the tubing. Thus, if a force, either external or internal to the administration set or cartridge 500, is exhibited on the tubing, rather than the force being directly on the coupling of the two types of tube at or near either the entry port 435 or exit port 440, the strain relief path disperses the force along a greater distance of tubing and also indirectly so as to minimize the risk of the tubes becoming decoupled. To further assist in decoupling prevention, an entry crimp point 445 and/or an exit crimp point 450 may be used. Such crimp points may comprise raised ridges or portions of the administration set or cartridge 500 casing that pinch the two types of tubing together at their point of coupling and providing a force perpendicular to any likely decoupling force. Thus, the likelihood of the two types of tube decoupling is further decreased, thereby ensuring the safety and consistency of the system's operation.

Figure 4:
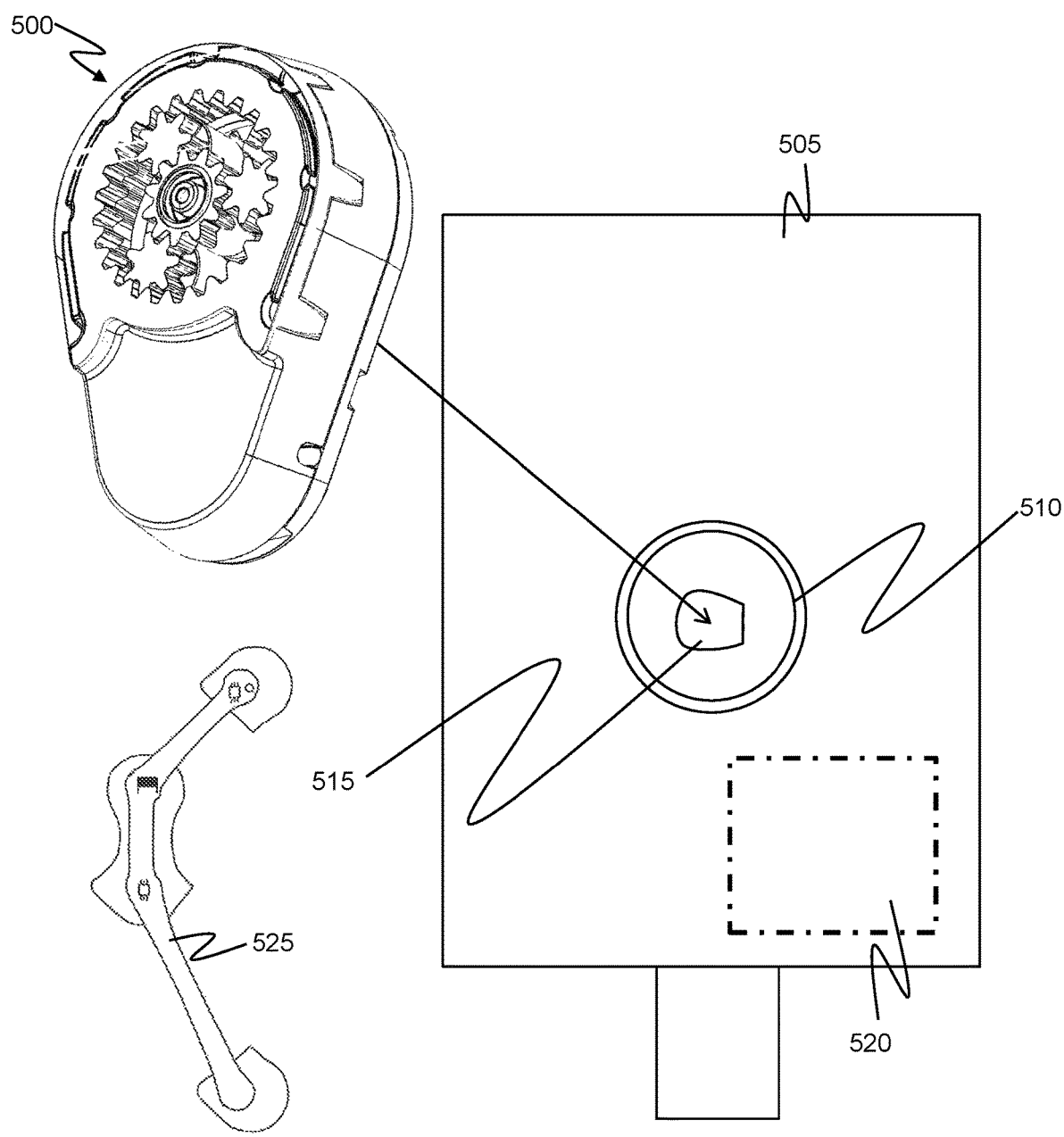
FIG. 4. Diagram depicting various components of the present invention including an administration set/cartridge, a pump module, and a physiological signal sensor.

FIG. 4 depicts the administration set/cartridge 500 in relation to the pump module 505 onto which it is adapted to be placed. As previously noted, the pump module 505 may comprise a raised portion or ridge 510 onto which a locator ring (FIG. 3B, 345) can be placed in order to situate and fit together the administration set/cartridge 500 and the pump module 505. The pump module 505 further comprises a driver shaft or driver 515 and a driver motor 520 as disclosed in relation to FIG. 2 above. Additionally, a physiological signal sensor is depicted in the optional form of an electrode array, and particularly an EEG array such as is disclosed in parent U.S. patent application Ser. No. 14/874,736.

While a preferred embodiment is disclosed herein, it will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed:

1. A system for delivering intravenous drugs and fluids to a subject, the system comprising:
    an infusion pump comprising
    an administration set integrating a disposable cartridge comprising at least two rollers or roller elements, gears, a tube, and a pumping chamber having an entry opening, an exit opening, and a tubing groove having a groove wall with a non-concentric geometry against which the tube is being occluded by a passage of the at least two rollers or roller elements, and where the non-concentric geometry of the tubing groove is such that a distance between each of the at least two rollers or roller elements and the groove wall with respect to the at least two rollers or roller elements is adapted to reduce flow pulsation and occlusion; and
    a pump module comprising a driving shaft adapted to cause the gears to rotate, the pump module adapted to allow the disposable cartridge to be inserted on to the pump module and locked into place;
    a physiological signal sensor adapted to acquire a physiological signal from the subject; and
    a controller adapted to control the infusion pump and administration of an anesthetic or sedative, the controller comprising a processor adapted for receiving the physiological signal from the physiological signal sensor and further comprising an algorithm adapted to perform real-time quantitative monitoring of the physiological signal,
    wherein the infusion pump is adapted to progressively increase occlusion at or near the entry opening and progressively decrease occlusion at or near the exit opening and to reduce flow pulsation.

2. The system in claim 1, wherein the controller is adapted to calculate safety limits directly calculated based on one or more of the subject's weight, age, height, gender and overall health status.

3. A system for delivering intravenous drugs and fluids to a subject, the system comprising:
    an infusion pump comprising
    an administration set integrating a cartridge comprising at least two rollers or roller elements, gears, a tube, and a pumping chamber having an entry opening, an exit opening, and a tubing groove having a groove wall with a non-concentric geometry against which the tube is being occluded by a passage of the at least two rollers or roller elements, and where the non-concentric geometry of the tubing groove is such that a distance between each of the at least two rollers or roller elements and the groove wall with respect to the at least two rollers or roller elements is adapted to reduce flow pulsation and occlusion; and
    a pump module comprising a driving shaft adapted to cause the gears to rotate, the pump module adapted to allow the cartridge to be inserted on to the pump module and locked into place; and
    a physiological signal sensor adapted to acquire a physiological signal from the subject; and a controller adapted to control the infusion pump and administration of an anesthetic or sedative, the controller comprising a processor adapted for receiving the physiological signal from the physiological signal sensor and further comprising an algorithm adapted to perform real-time quantitative monitoring of the physiological signal,
    wherein the infusion pump is adapted to progressively increase occlusion at or near the entry opening and progressively decrease occlusion at or near the exit opening and to reduce flow pulsation.

4. The system in claim 3, the system further including an anti-free-flow device adapted to prevent blood from draining from the subject, or prevent the intravenous drugs from freely entering the subject, when the infusion pump is being set up; and a pressure sensor to detect occlusion.

5. The system in claim 3, wherein the algorithm of the controller is adapted to calculate a cortical index of a level of consciousness of the subject and the infusion pump is adjusted based at least in part on the calculated cortical index.

6. The system in claim 4, wherein the controller of the system is adapted to operate to detect a brain dysfunction or injury within 15 seconds of application of the system and/or an occurrence of the brain dysfunction or injury.

* * * * *